(12) United States Patent
Whiting et al.

(10) Patent No.: US 11,324,825 B2
(45) Date of Patent: May 10, 2022

(54) SYNTHETIC RETINOIDS (IN CELL MODULATION)

(71) Applicant: University of Durham, Durham (GB)

(72) Inventors: Andrew Whiting, Durham (GB); Carrie Ambler, Durham (GB); Mark Coles, York (GB); David Chisholm, Durham (GB)

(73) Assignee: UNIVERSITY OF DURHAM

( * ) Notice: Subject to any disclaimer, the term of this patent is extended or adjusted under 35 U.S.C. 154(b) by 0 days.

(21) Appl. No.: 16/357,755

(22) Filed: Mar. 19, 2019

(65) Prior Publication Data

US 2019/0209685 A1 Jul. 11, 2019

Related U.S. Application Data

(63) Continuation of application No. 16/323,924, filed as application No. PCT/GB2017/052351 on Aug. 9, 2017.

(30) Foreign Application Priority Data

Aug. 9, 2016 (GB) ...................................... 1613712

(51) Int. Cl.

| | |
|---|---|
| A61K 31/47 | (2006.01) |
| A61K 41/00 | (2020.01) |
| A61K 31/435 | (2006.01) |
| A61K 47/55 | (2017.01) |
| A61P 17/06 | (2006.01) |
| A61P 31/12 | (2006.01) |
| A61P 31/04 | (2006.01) |
| A61P 31/10 | (2006.01) |
| A61P 35/00 | (2006.01) |
| A61K 31/07 | (2006.01) |

(52) U.S. Cl.
CPC .......... *A61K 41/0057* (2013.01); *A61K 31/07* (2013.01); *A61K 31/435* (2013.01); *A61K 31/47* (2013.01); *A61K 47/551* (2017.08); *A61P 17/06* (2018.01); *A61P 31/04* (2018.01); *A61P 31/10* (2018.01); *A61P 31/12* (2018.01); *A61P 35/00* (2018.01)

(58) Field of Classification Search
CPC .............................. C07D 215/06; A61K 31/47
See application file for complete search history.

(56) References Cited

U.S. PATENT DOCUMENTS

| 10,759,762 B2 * | 9/2020 | Whiting .................. A61P 17/06 |
| 2017/0217893 A1 * | 8/2017 | Whiting ............... C07D 215/06 |

FOREIGN PATENT DOCUMENTS

| DE | 3115871 A1 | 1/1982 |
| WO | 2008/025965 A2 | 3/2008 |
| WO | 2008/056567 A1 | 2/2010 |
| WO | 2016/055800 A2 | 4/2016 |
| WO | 20166/055800 A2 | 4/2016 |

OTHER PUBLICATIONS

Chrisloforou et al., "The Application of the Hammett Equation to 13C.N.M.R. Spectrometry. The Transmission of Electronic Effects through Azophenylene and Elhenylphenylene Groups"; Aust. J of Chem., 1982, 35:729-738.

Comitato et al., "Impairment of Spermatogenesis and Enhancement of Testicular Germ Cell Apoptosis Induced by Exogenous All-Trans-Relinoic Acid in Adult Lizard Podarcis sicula", Journal of Experimental Zoology, 305A:288-298 2006).

Donnelly et al., "Derivatives of 5-Aminolevulinic Acid for Pholodynamic Therapy", Perspectives in Medicinal Chemistry 2007; 1 :49-63.

Elhirajan et al., "The role of porphyrin chemistry in tumor imaging and pholodynamic therapy", Chem. Soc. Rev., 2011, 10:340-362.

Grether-Beck et al., "Activation of transcription factor AP-2 mediates UVA radiation-and singlet oxygen-induced expression of the human intercelllular adhesion molecule 1 gene", Proc. Nall. Acad. Sci. USA, 93:14586-14591, 1996.

Josefsen et al., "Pholodynamic Therapy and the Development of Metal-Based Photosensitisers", Metal-Based Drugs, vol. 2008, Article ID 276109, 24 pages; Published online Sep. 11, 2008; doi:10.1155/2008/276109.

Klikar et al., "N,N'-Dibutylbarbituric acid as an acceptor moiety in push-pull chromophores", New J Chem., 2013, 37:4230-4240.

Lanoe et al., "Two photon sensitizers for PDT: molecular engineering towards understanding of their excited state photophysics"; Proc, of SPIE, 8545:85408-1-85408-7,2012.

Lartillot et al., "On the photobiological Properties of Chimeras Combining Quartery Ammonium Derivatives of Retinoid Amides and Psoralen. A Study with Cultured Human Keratinocytes", Photochemistry and Photobiology, 2003, 78 (6):623-632.

Lee et al., "Relinoid-Responsive Transcriptional Changes in Epidermal Keratinocytes", Journal of Cellular Physiology, 220:427-439, 2009.

Mfouo-Tynga et al., "Cell Death Pathways and Phthalocyanine as an Efficient Agent for Pholodynamic Cancer Therapy", Int. J Mol. Sci., 2015, 16:10228-10241.

Motoshima et al., Peroxisome proliferator-activated receptor agonists with phenethylphenylphthalimide skeleton derived from thalidomide-related liver X receptor antagonists: Relationship between absolute configuration and subtype selectivity, Bioorganic & Medicinal Chemistry, 2011, 19:3156-3172.

Picard et al., "8-Br-quinoline derivatives as sensitizers combining two photon induced fluorescence and singlet oxygen Jene ration", Tetrahedron 71: 1088-1094 (2015).

Simon et al., "Role of reactive oxygen species {ROS) in apoptosis induction", Apoptosis, 2000, 5:415-418.

Wang et al., "Ultraviolet irradiation of human skin causes functional vitamin A deficiency, preventable by all-trans retinoic acid pre-treatment", Nature Medicine, 5(4):418-422, 1999.

* cited by examiner

*Primary Examiner* — Rei Tsang Shiao
(74) *Attorney, Agent, or Firm* — K&L Gates LLP

(57) ABSTRACT

There are described novel compounds of formula I: (I) in which, in which $A^1$, $A^2$, $A^3$, $A^4$, $R^1$ and $R^2$ are each as herein defined, for use in the treatment or alleviation of an RAR mediated condition; and methods related thereto.

17 Claims, 19 Drawing Sheets

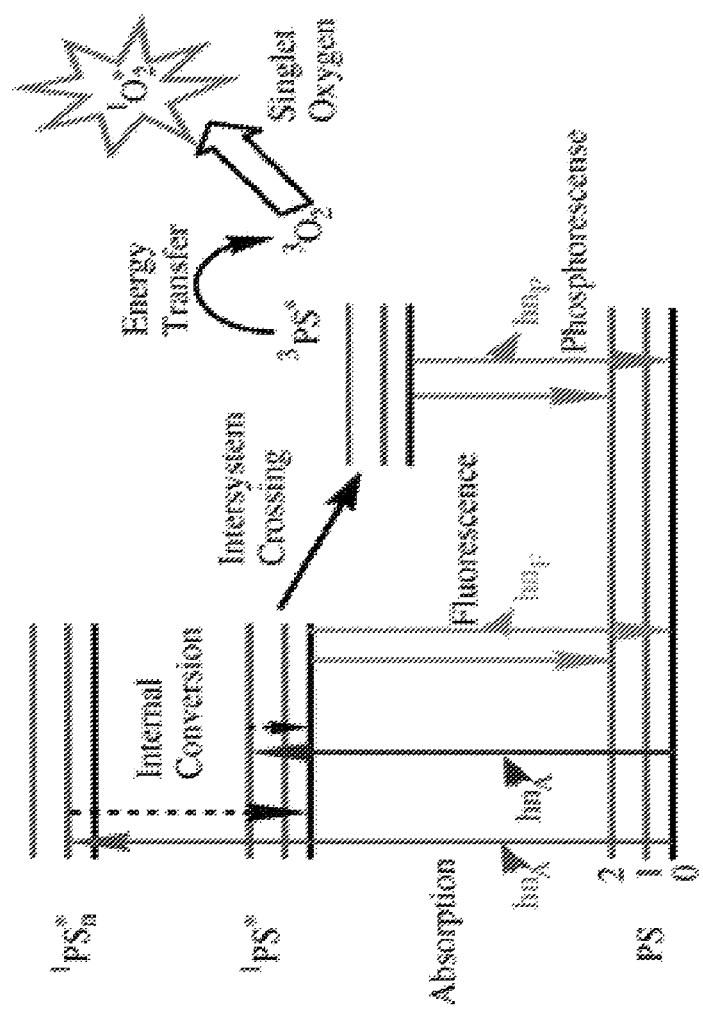
Figure 1: Jablonski diagram showing the formation of singlet oxygen.

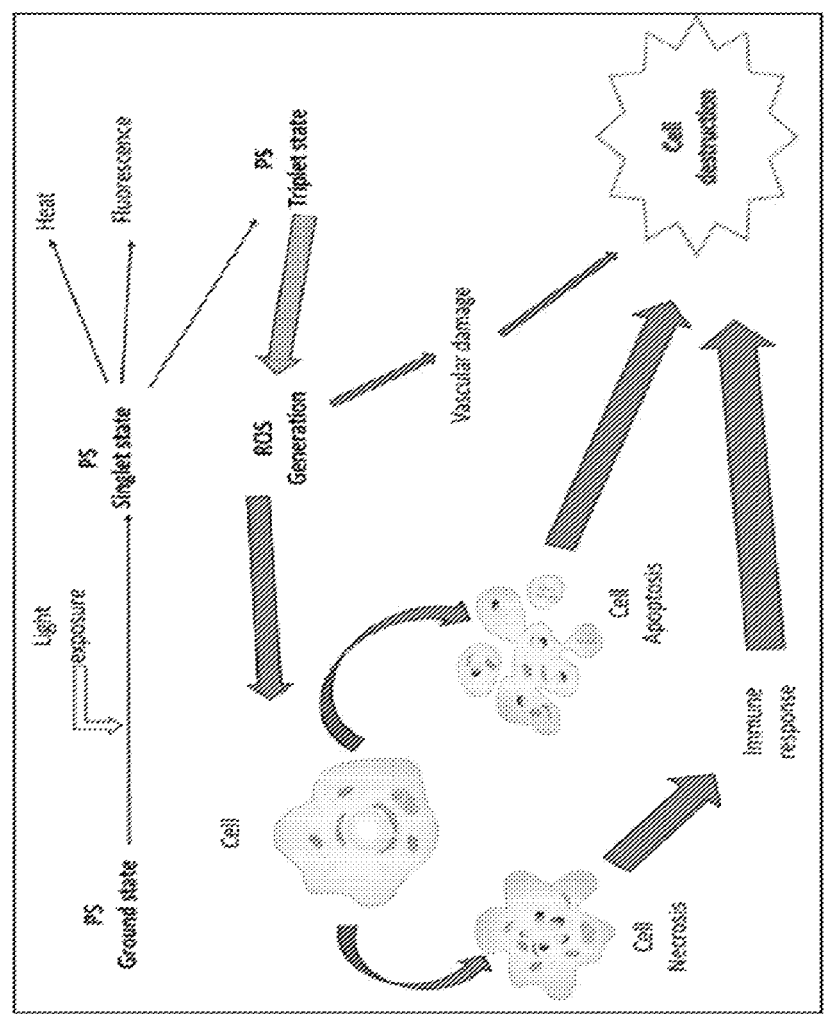
Figure 2: The biological effects of ROS generation.

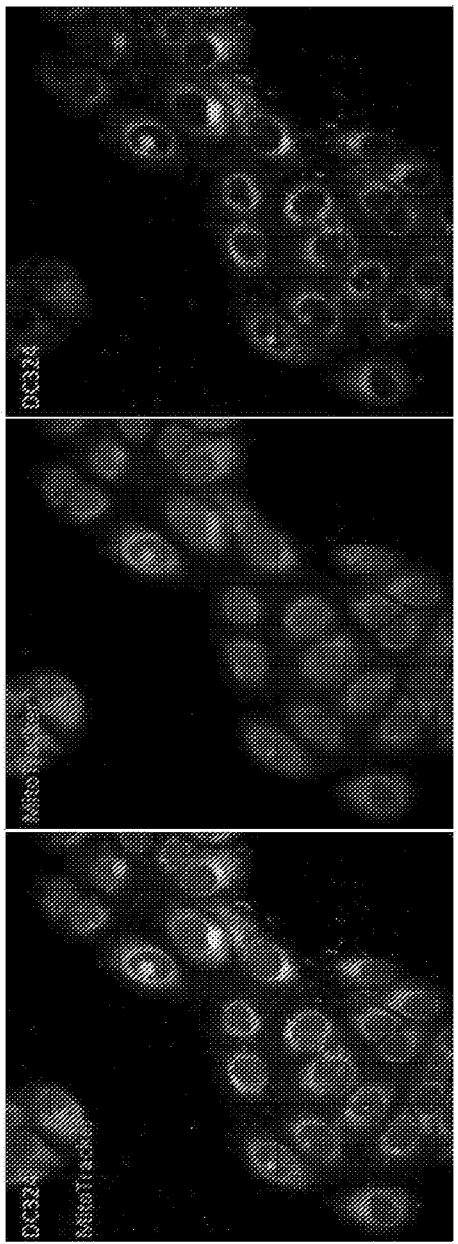
Figure 3: DC324 localised to one side of the nucleus in large patches of cells.
Figure 4: DC324 co-imaged with BODIPY® Golgi stain.

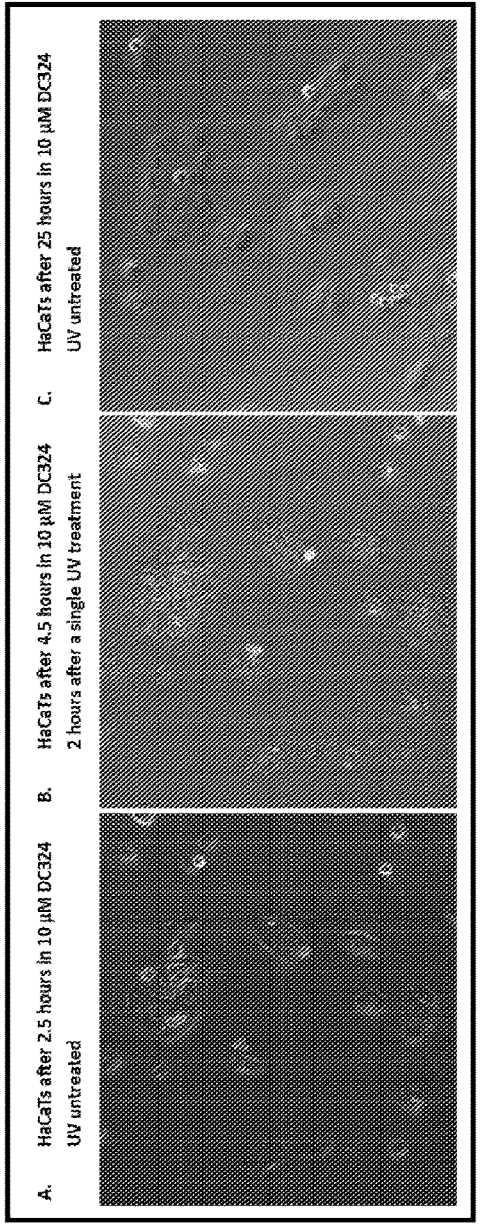
Figure 5: DC324 was the most rapid inducer of cell death.
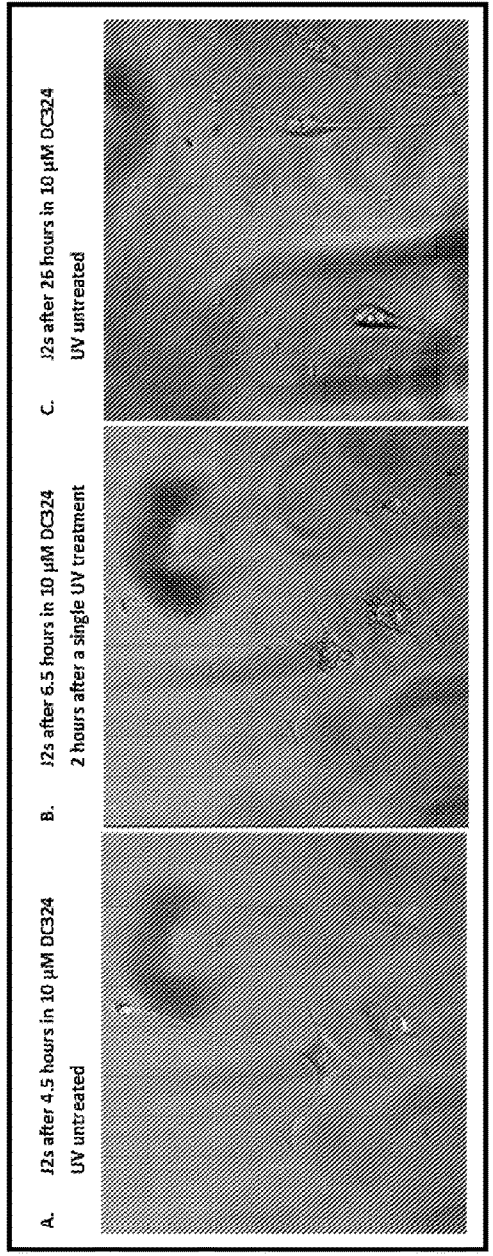
Figure 6: Cell death observations were consistent across different cell lines.

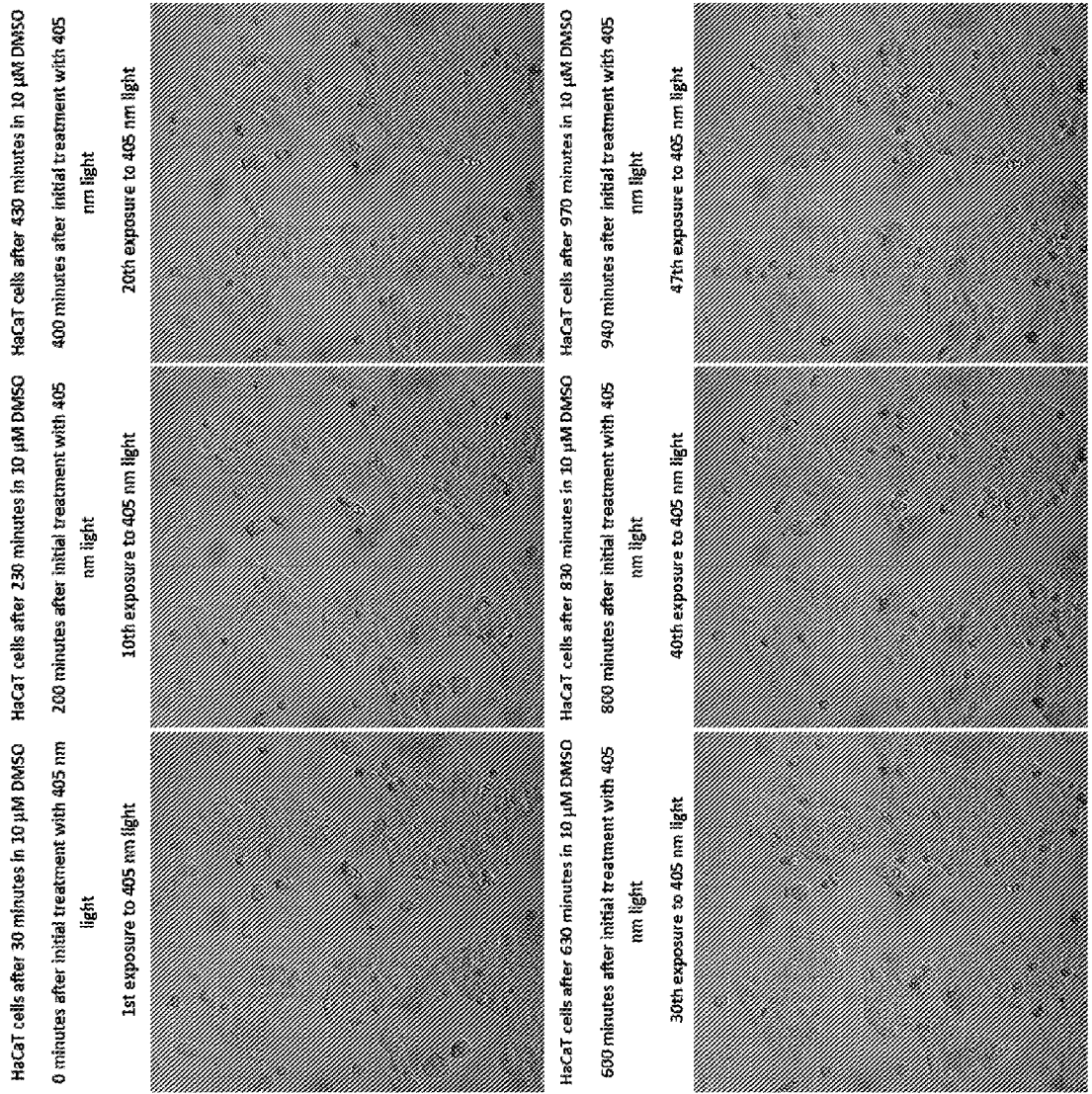
Figure 7: The majority of DMSO treated cells appeared healthy after 47 exposures to 405 nm laser, at 50% strength.

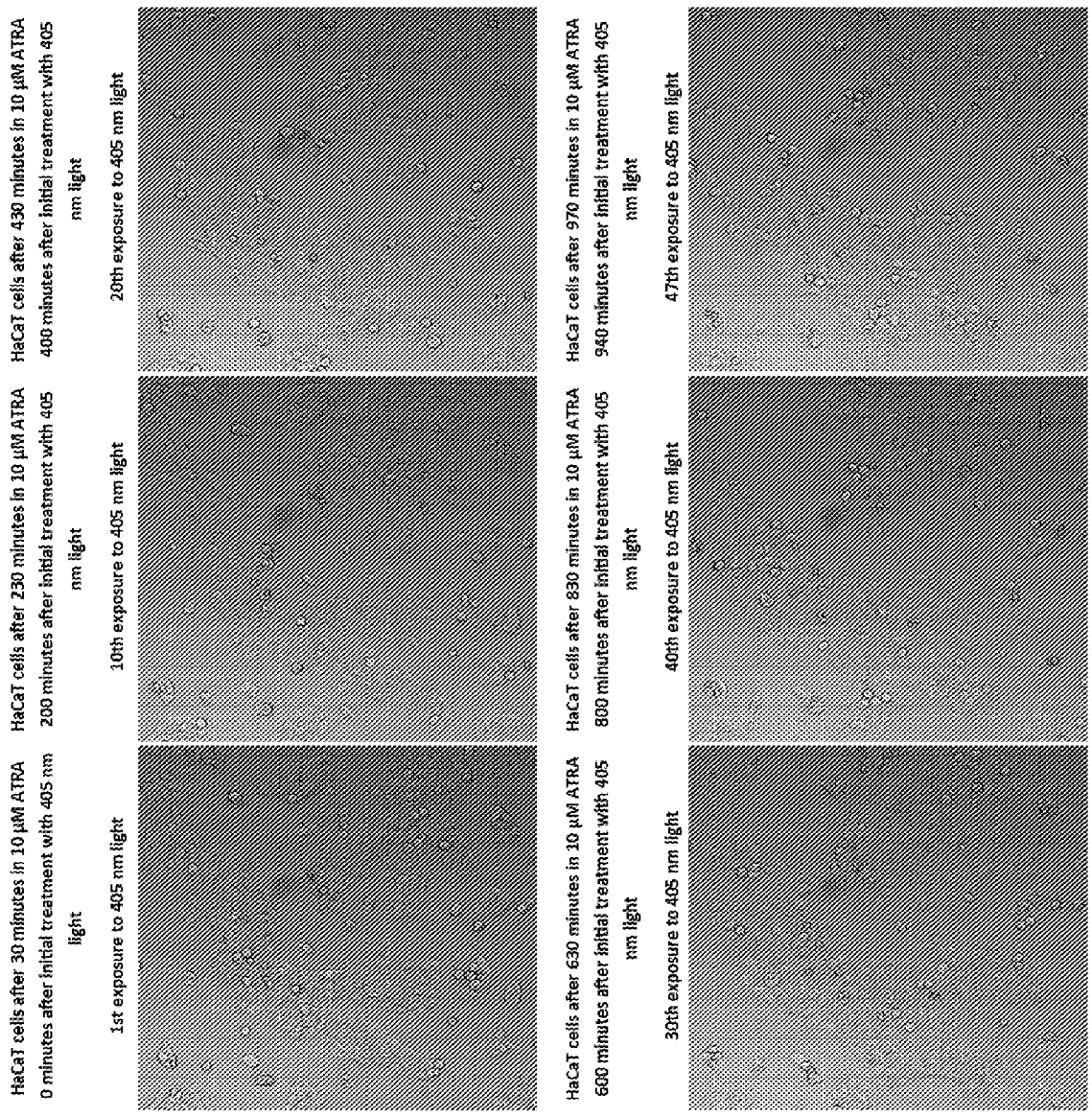
Figure 8: The majority of ATRA treated cells appeared healthy after 47 exposures to 405 nm laser, at 50% strength.

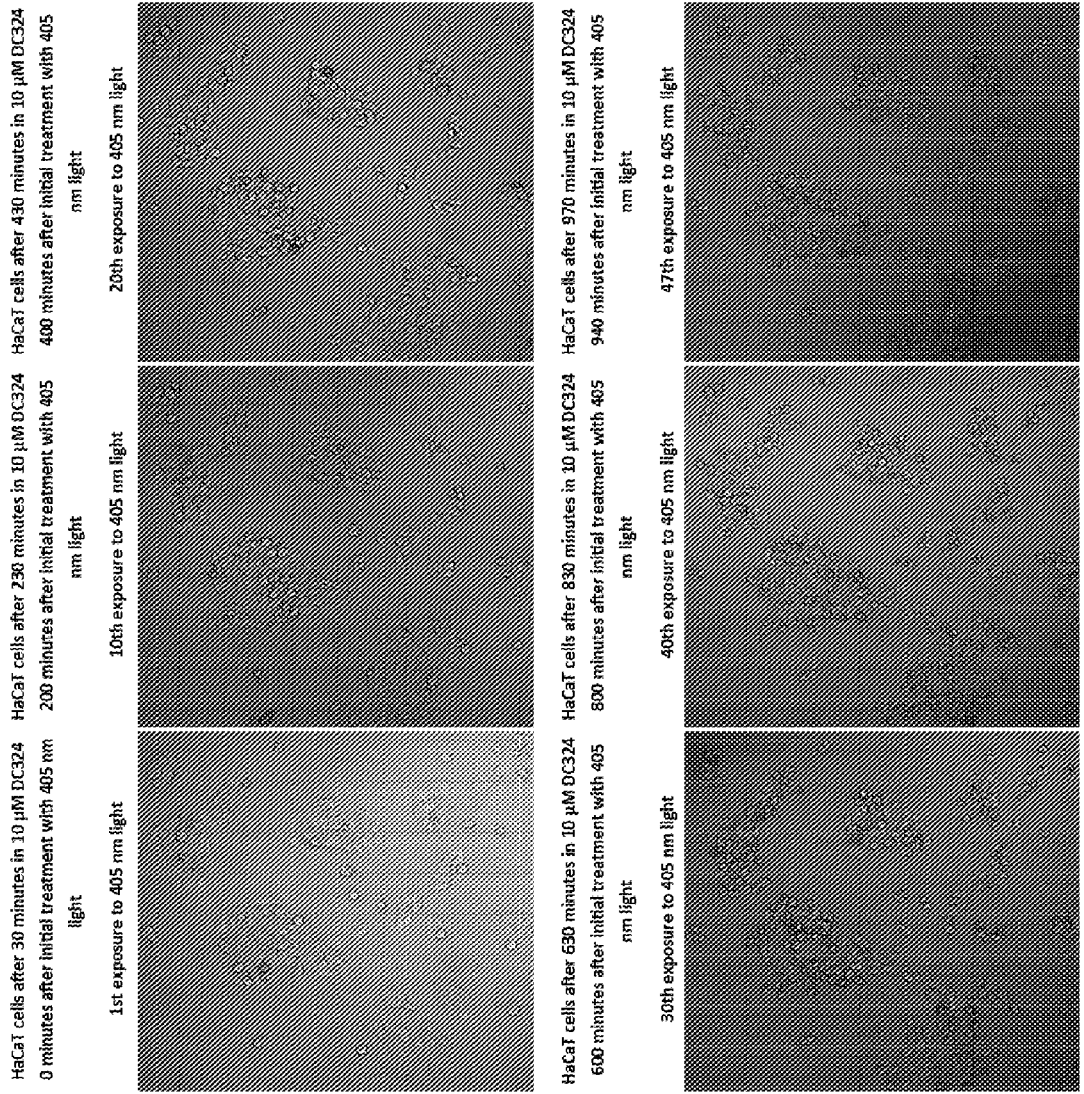
Figure 9: Membrane blebbing was induced in DC324 treated cells by 405 nm laser, at 50% strength.

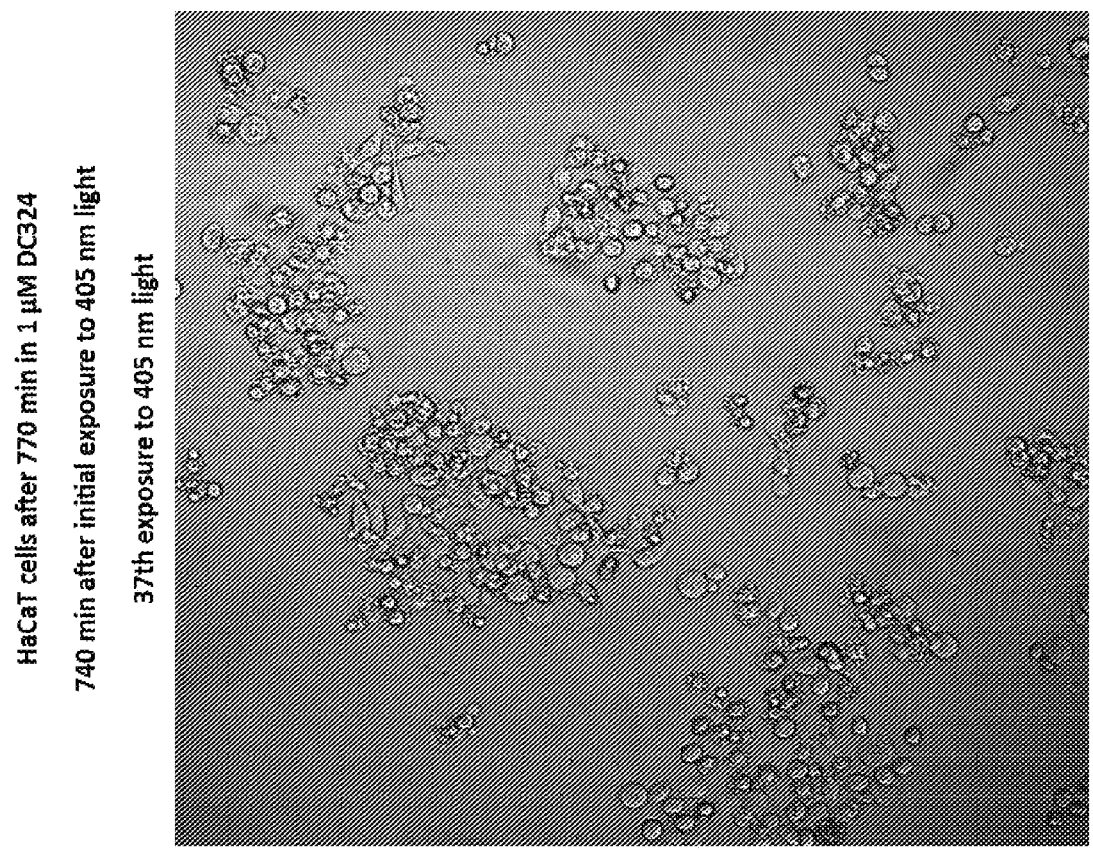
Figure 10: DC324 treated cells putatively producing apoptotic bodies.

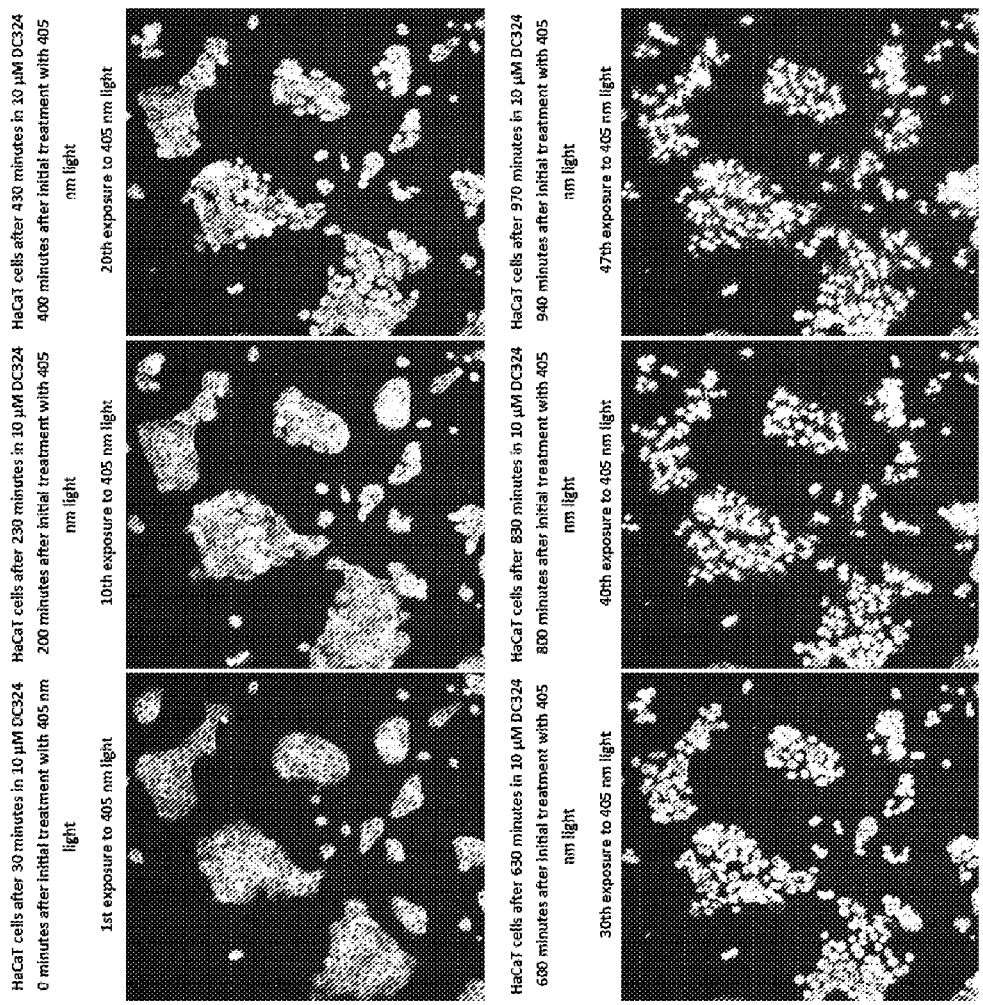
Figure 11: DC324 fluorescence from treated HaCaT cells, imaged with 405 nm laser light, at 50% strength.

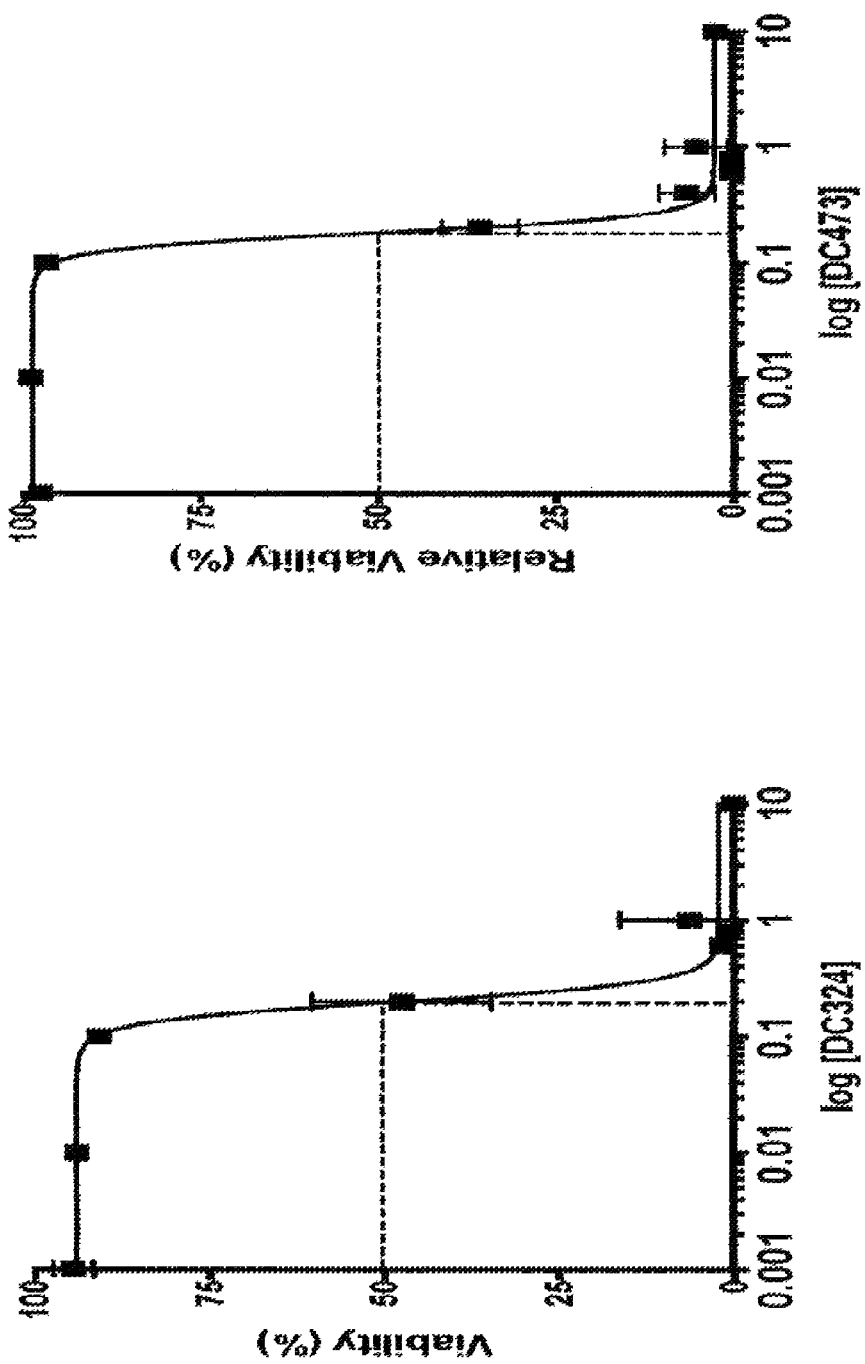
Figure 12: The dose-dependent response of HaCaT cells treated with DC324 and DC473 and 10 seconds of UV.

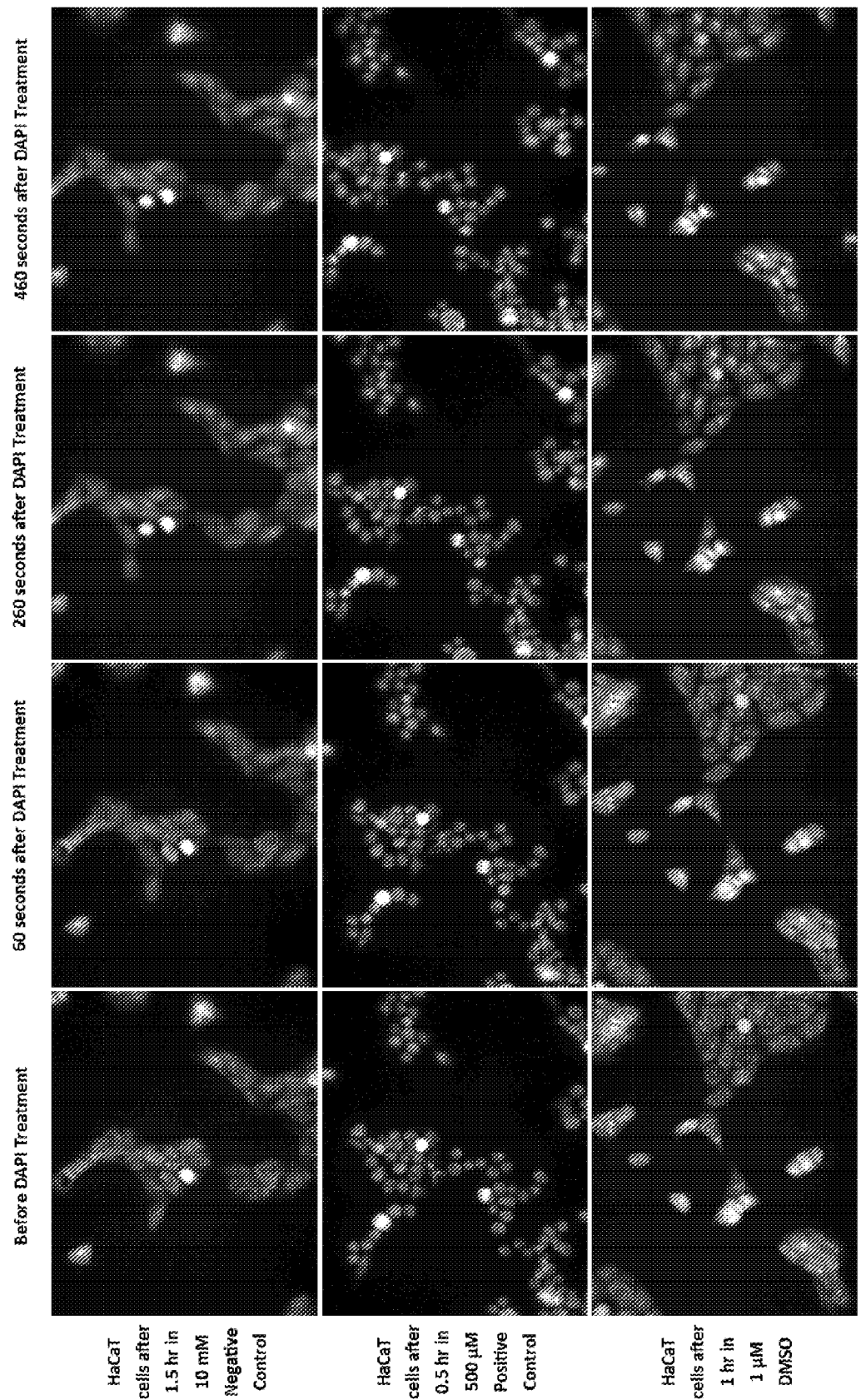
Figure 13: Control treatments stained for superoxide after exposure to UV.

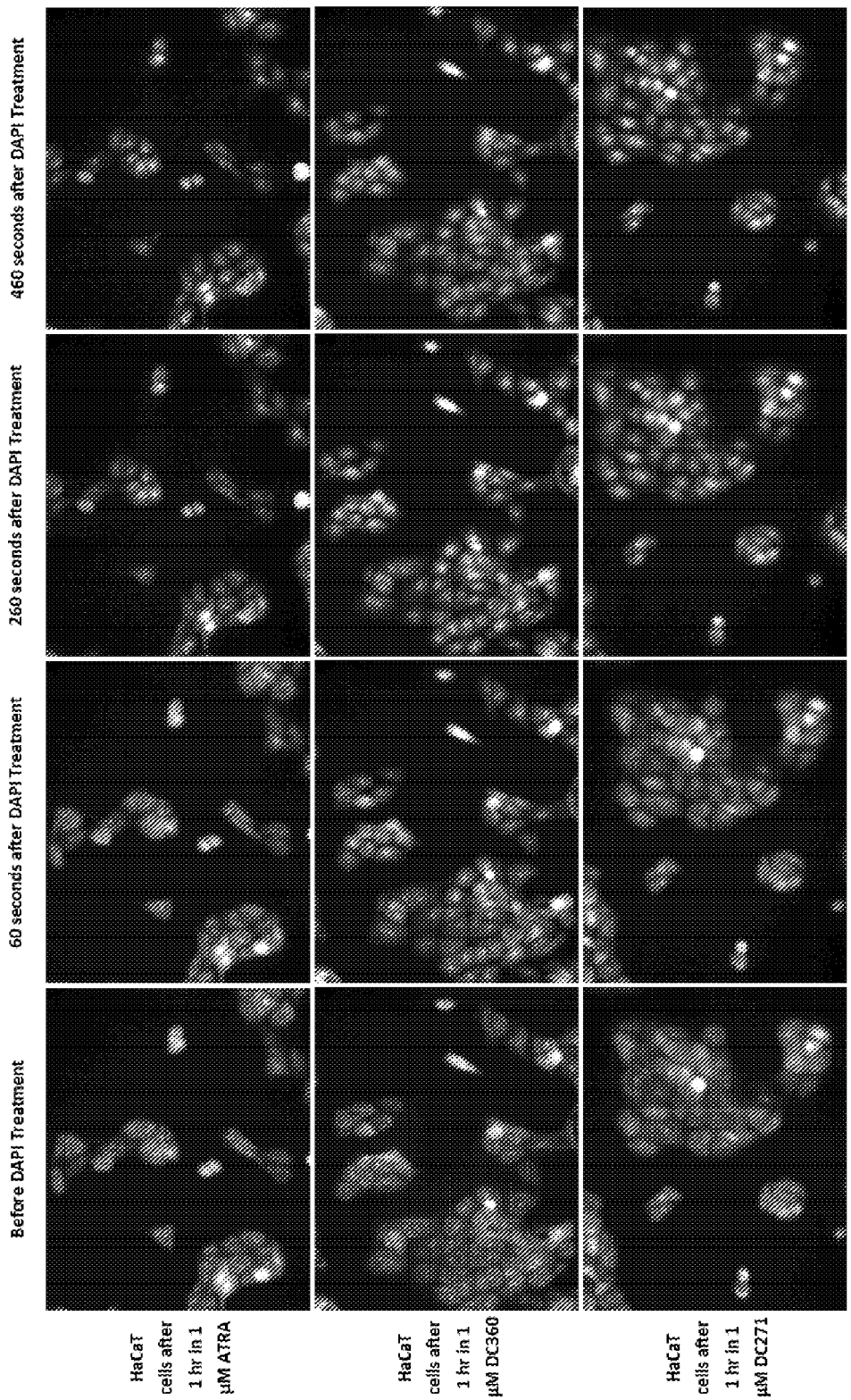
Figure 14: Active compounds stained for superoxide after exposure to DAPI.

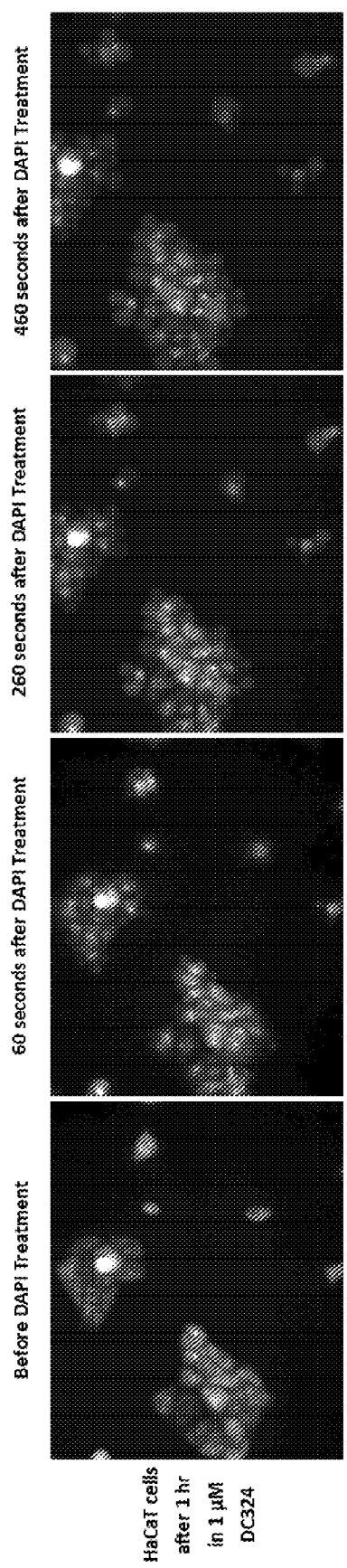
Figure 15: Inactive DC324 compound treated cells stained for superoxide after UV exposure.

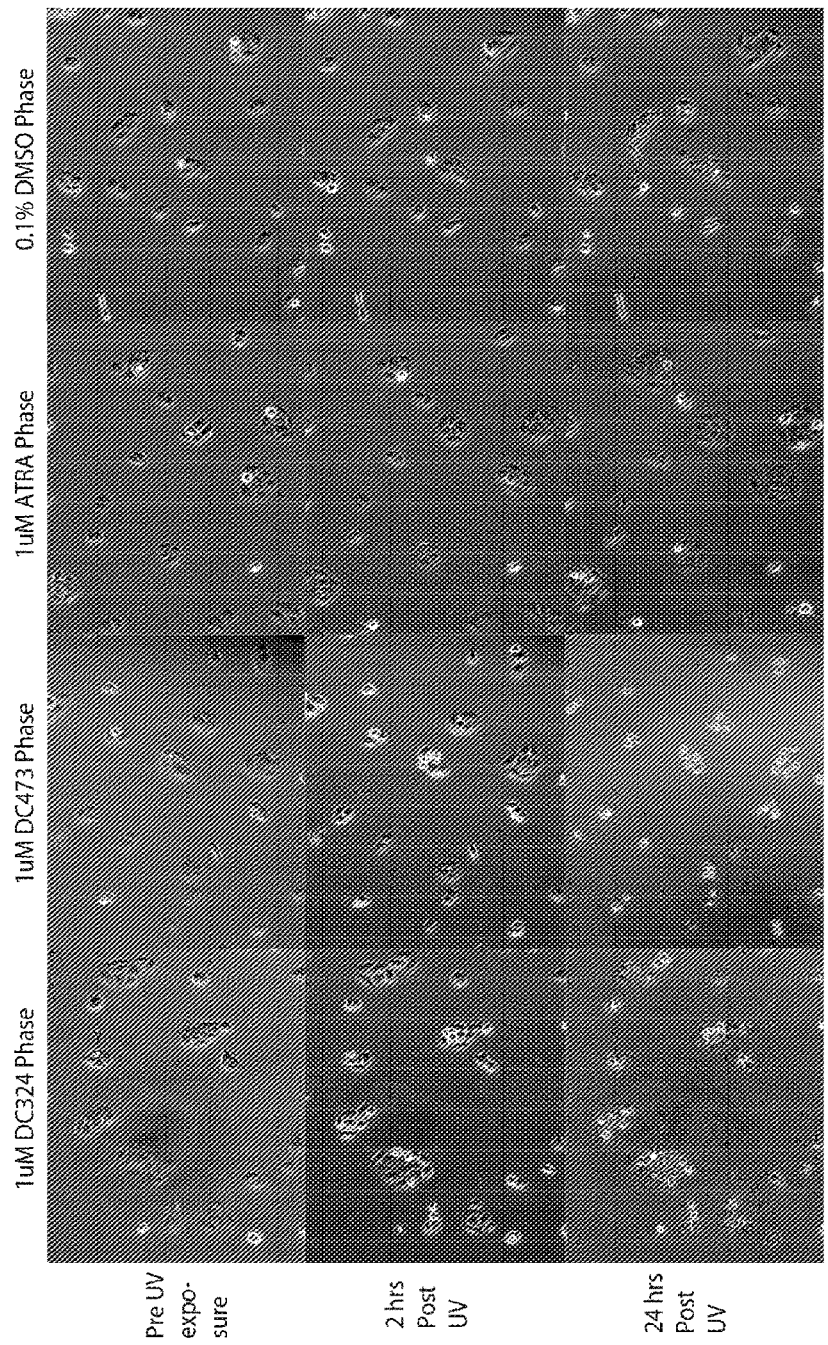
Figure 16: DC473 compound treated cells after 2 hours and 24 hours UV exposure.

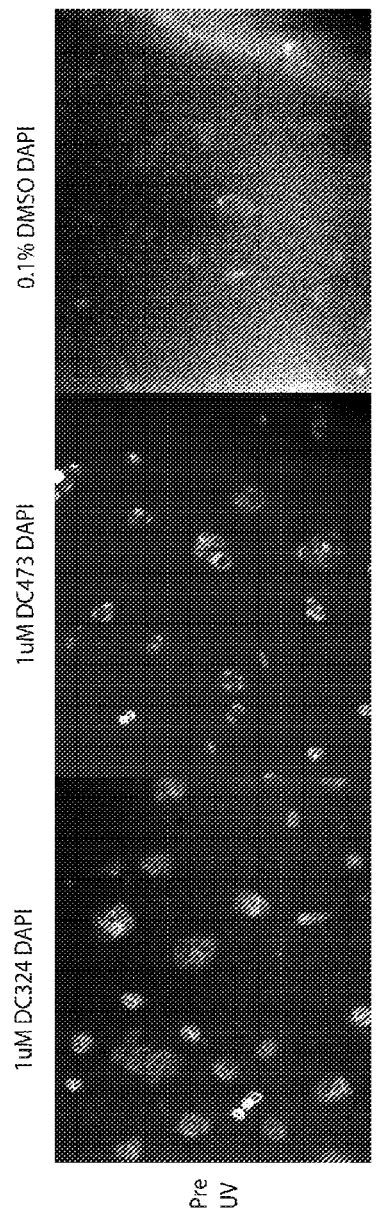
Figure 17: Comparison of DC324 and DC473 compound treated cells.

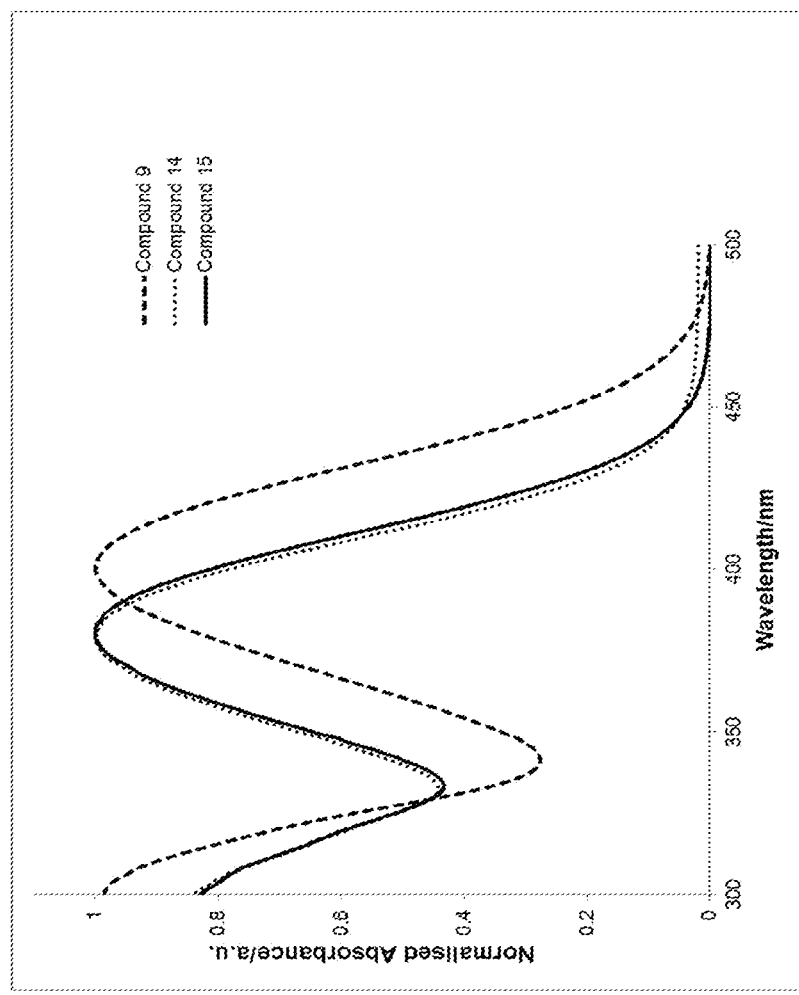
Figure 18: Normalised absorbance spectra of compounds 9 (DC324), 14 (DC473) and 15 (DC474) in $CHCl_3$ (10 μM).

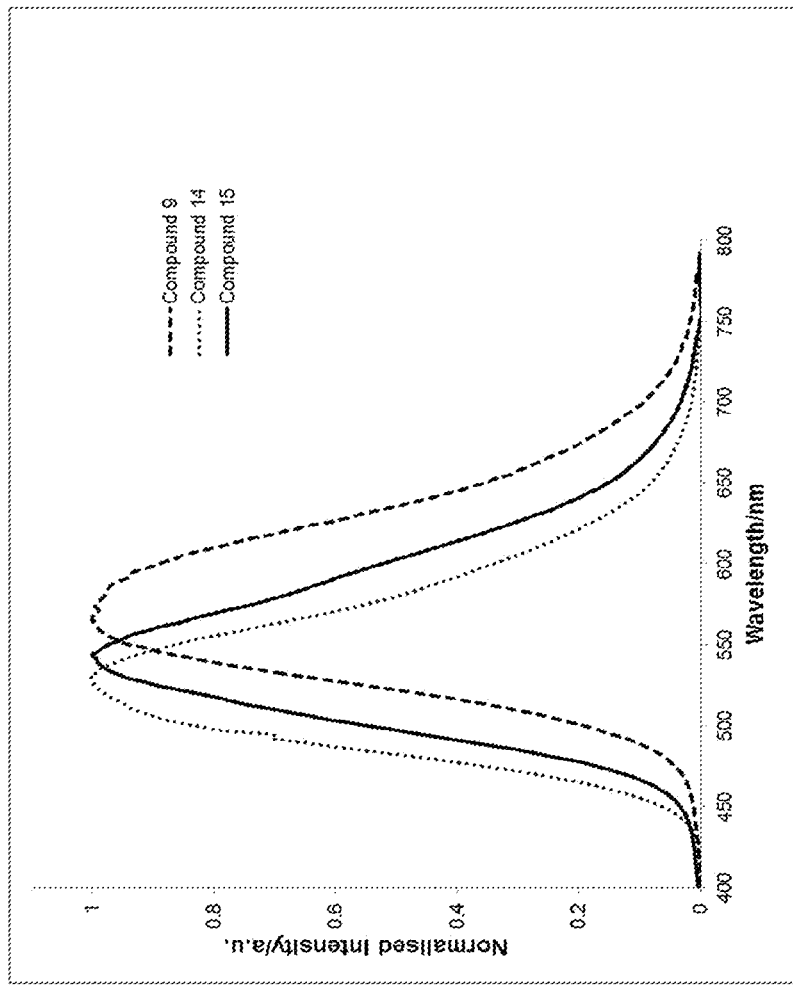
Figure 19: Normalised emission spectra of compounds 9 (DC324), 14 (DC473) and 15 (DC474) in $CHCl_3$ (100 nM), with excitation at their respective maximal absorption wavelengths.

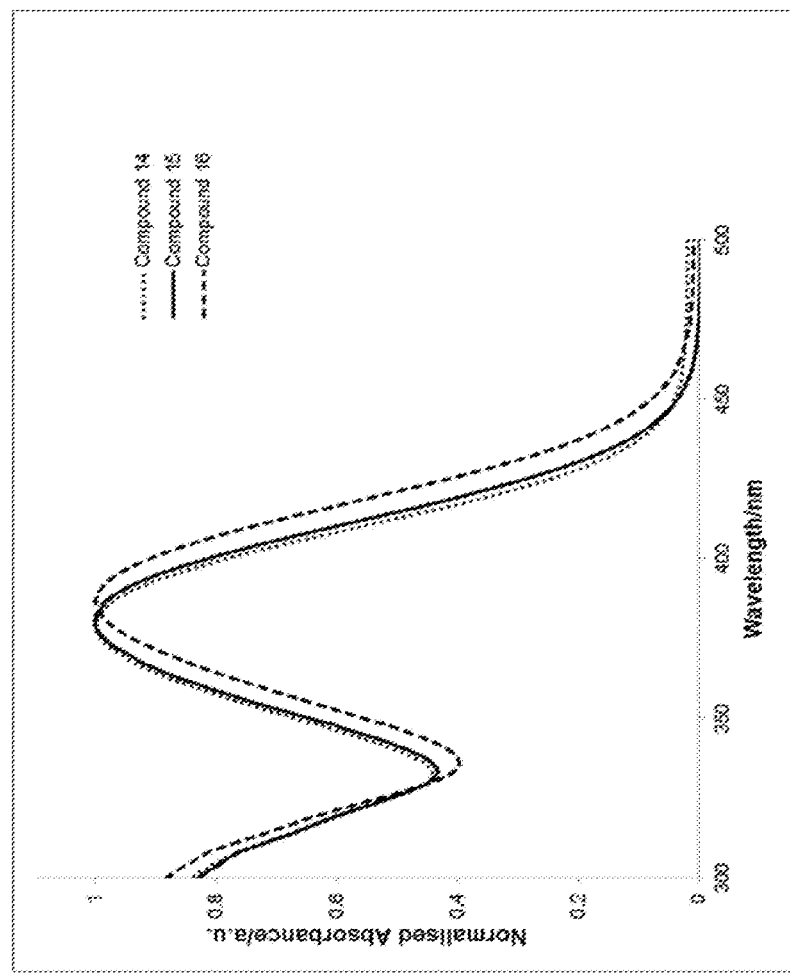
Figure 20: Normalised absorbance spectra of compounds 14 (DC473), 15 (DC474) and 16 in CHCl$_3$ (10 μM).

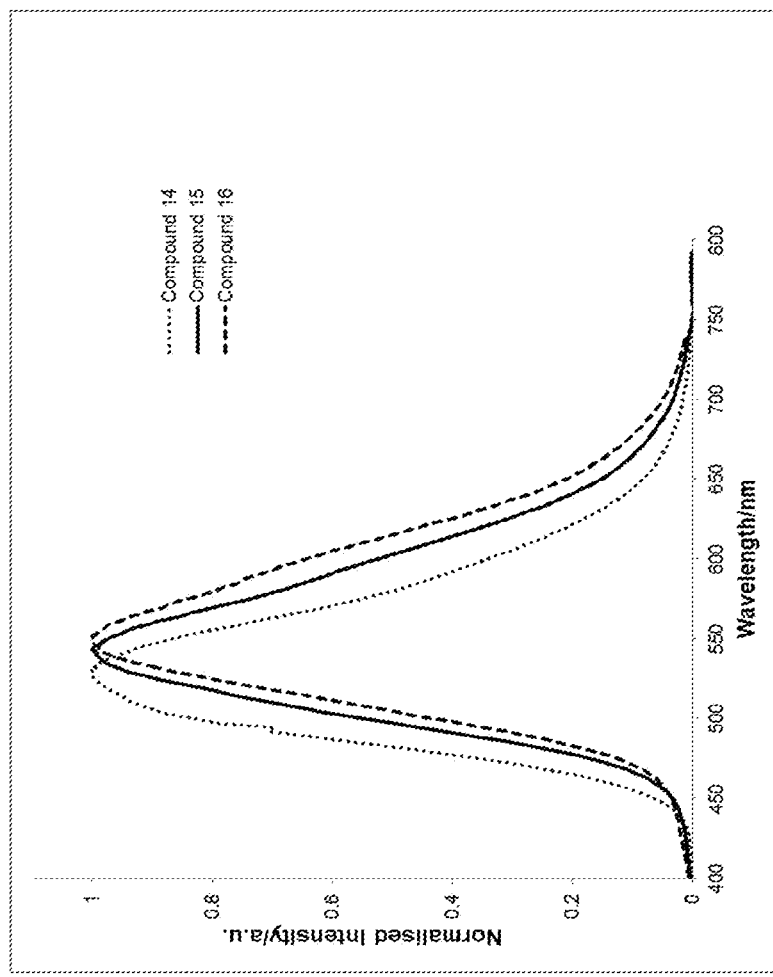
Figure 21: Normalised emission spectra of compounds 14 (DC473), 15 (DC474) and 16 in CHCl₃ (100 nM), with excitation at their respective maximal absorption wavelengths.

SYNTHETIC RETINOIDS (IN CELL MODULATION)

CROSS REFERENCE TO RELATED APPLICATIONS

The present application is a continuation application of U.S. patent application Ser. No. 16/323,924 filed Feb. 7, 2019, which is a national phase under 35 U.S.C. § 371 of International Patent Application No. PCT/GB2017/052351 filed on Aug. 9, 2017, which claims priority to and benefit of United Kingdom Patent Application No. 1613712.7 filed on Aug. 9, 2016. Each of the forgoing applications is hereby incorporated by reference in its entirety into the present application.

FIELD OF THE INVENTION

The present invention relates to a novel use of compounds and methods of treatment related thereto. In one aspect the invention also relates to certain compounds that are novel per se.

More particularly, the present invention relates to the use of highly conjugated synthetic retinoid compounds in the generation of reactive oxygen species and the destruction of cells. The invention also provides a method of medical treatment using the novel compounds of the invention, for example in a photodynamic therapy.

BACKGROUND TO THE INVENTION

Vitamin A (retinol) and its derivatives belong to a class of compounds known as retinoids. Retinoids are an important class of signalling molecules that are involved in controlling many important biological pathways from embryogenesis through to adult homeostasis and many aspects of stem cell development, such as, stem cell proliferation, differentiation and apoptosis.

Retinoids are structurally and/or functionally related to vitamin A; and many possess biological activity including all-trans-retinoic acid (ATRA). ATRA is the most abundant endogenous retinoid and has been widely studied for many years; ATRA isomerises under physiological and experimental conditions, with different isomers activating different receptors, thus accounting for the variety of biological effects observed with these small molecules.

Due to the ability of retinoids to control differentiation and apoptosis in both normal and tumour cells, they have the potential to act as chemopreventative and chemotherapeutic agents, although toxicity has prevented widespread use.

However, ATRA exhibits poor stability, in particular upon exposure to light. ATRA compounds isomerise and degrade upon exposure to light. To overcome this, efforts are made to store and work with ATRA in the dark, but such precautions increase the cost associated with working with ATRA, and do not entirely mitigate the problem. Furthermore, as ATRA is liable to photoisomerisation and degradation upon storage, it is difficult to predict accurately the amount of active compound administered in a single dose. Efforts have been made to overcome the problems associated with ATRA by synthesising stable retinoid compounds. It is generally believed that ATRA is susceptible to photoisomerisation due to its conjugated linker group.

International Patent application No. PCT/GB2007/003237 (WO 2008/025965) disclosed new retinoid compounds which exhibited good stability and induced cell differentiation.

Apoptosis is a programmed energy-requiring form of cell death, involving the activation of a number of proteases called 'caspases'. The induction of apoptosis by ATRA is well documented in the literature. ATRA can trigger both the induction and suppression of pro-apoptotic genes, as well as the suppression of several anti-apoptotic genes, leading to an overall promotion of apoptosis.[1,2] ATRA can induce cell proliferation. However, the pro-apoptotic effect of ATRA is concentration dependent.

Unlike endogenous ATRA, the synthetic retinoids are stable and do not break down easily.

Triplet state photosensitizers (PS) usually contain a light-harvesting region, which is responsible for the dual-functionality of light-harvesting and intersystem crossing, where electrons in the singlet state non-radiatively pass to the triplet state. Quenching of the triplet-excited state can result in the formation of reactive oxygen species (ROS), radicals from ground state molecular oxygen or direct chemical reactions with surrounding molecules. High levels of ROS act as a non-selective, highly effective killer of animal, plant, fungal and bacterial cells. Localised ROS production is an immune defence strategy employed in both animal and plant systems in response to pathogen attack.

However, whilst photoactive compounds are known, most suffer from a number of drawbacks which make them poor therapeutic agents. Firstly, many exhibit inadequate pharmacological properties, such as poor aqueous solubility and long biological half-lives, which causes skin photosensitivity for weeks post-treatment. In addition, many lack, or exhibit poor ability to target specific tissues or cells, often resulting in significant off-target damage. Existing photoactive compounds used for the production of ROS in vivo are also, typically, high molecular weight polymers of varying length, making consistent manufacture difficult, or contain metals including zinc, palladium, indium, tin or lutetium, which may cause toxicity issues.[8,9]

International Patent application No. WO 2016/055800 describes a series of synthetic, fluorescent small molecules that act as triplet state photosensitizers when activated by UV or violet (405 nm) light.

The present invention pertains to related synthetic retinoid compounds with a highly conjugated structure.

Due to the incorporation of an electron donating group, typically a nitrogen, the highly conjugated retinoid compounds may be biologically inert in the unactivated state, but in the activated state, e.g. by exposure to pulses of low to medium energy short-wavelength visible light, can cause the apoptosis of cells.

Importantly, adjacent cells, not exposed to light are unharmed.

SUMMARY TO THE INVENTION

The present invention provides highly conjugated retinoid compounds suitable for use in, inter alia, photodynamic therapy.

Thus, according to a first aspect of the invention there is provided the use of a highly conjugated retinoid compound in the generation of reactive oxygen species when said compound is activated by light.

By the term "highly conjugated retinoid compound" is meant a compound that possesses a generally understood retinoid structure that includes at least six conjugated double or triple bonds or equivalents thereof. Such highly conjugated retinoid compound should be understood to possess an increased conjugation when compared to "normal" retinoids i.e. either natural retinoic acids or synthetic, direct analogues of retinoic acids, also referred to as synthetic retinoids and arotinoids.

For the avoidance of doubt reference to a retinoid should be construed as including naturally occurring compounds with a retinoid structure, synthetic retinoids and more conjugated homologues thereof. In addition, the term "retinoid" shall include arotinoids (aromatic retinoids).

More specifically, the present invention provides the use as herein described wherein the highly conjugated retinoid compound is a compound of formula I:

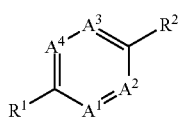

in which
$A^1$ is N or $CR^3$;
$A^2$ is N or $CR^4$;
$A^3$ is N or $CR^5$;
$A^4$ is N or $CR^6$;
$R^3$, $R^4$, $R^5$ and $R^6$, which may be the same or different, are each hydrogen, alkyl$_{C1-10}$, alkene$_{C2-12}$, aryl, aralkyl, halogen, trifluoroalkyl, cyano, nitro, —NR$^a$R$^b$, —OR$^a$, glycol, —C(O)R$^a$, —C(O)OR$^a$, —OC(O)R$^a$, —S(O)R$^a$R$^b$, —C(O)NR$^a$R$^b$ or a solubilising group;
$R^1$ is —NR$^{7a}$R$^{7b}$ or together with $R^6$ forms a ring II:

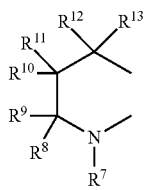

$R^7$ and $R^{7a}$ are each hydrogen, propynyl, —(CH$_2$)$_n$C≡CH, —(CH$_2$)$_n$SH, —(CH$_2$)$_n$SO$_2$F or —(CH$_2$)$_n$C═CH$_2$, alkyl$_{C1-10}$, said alkyl being optionally substituted by aryl or heteroaryl;
$R^{7b}$ is hydrogen, propynyl, alkyl$_{C1-10}$, said alkyl being optionally substituted by aryl or heteroaryl;
$R^8$, $R^9$, $R^{10}$ and $R^{11}$, which may be the same or different, are each hydrogen or alkyl$_{C1-4}$, aryl, halogen, trifluoroalkyl, —OR$^c$ or glycol, or together one pair of $R^8$ and $R^{10}$ or $R^9$ and $R^{11}$ represent a bond;
$R^{12}$ and $R^{13}$, which may be the same or different, are each hydrogen, alkyl$_{C1-4}$ or together one pair of $R^{10}$ and $R^{12}$ or $R^{11}$ and $R^{13}$ represent a bond, or $R^{12}$ and $R^{13}$ together form a group:

═CR$^{14}$R$^{15}$ provided that the pair of $R^{10}$ and $R^{12}$ or $R^{11}$ and $R^{13}$ does not represent a bond if a pair from $R^8$, $R^9$, $R^{10}$ and $R^{11}$ represents a bond;
$R^{14}$ and $R^{15}$, which may be the same or different, are each hydrogen or alkyl$_{C1-10}$; and
$R^a$, $R^b$ and $R^c$, which may be the same or different, are each hydrogen or alkyl$_{C1-10}$;
n is an integer from 1 to 6;

$R^2$ is a group III:

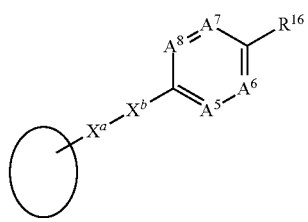

in which
$X^a$ is —C≡C—, —CH═CH— or —N═CH—;
$X^b$ is —C≡C— or is absent;
$A^5$ is N or $CR^{17}$;
$A^6$ is N or $CR^{18}$;
$A^7$ is N or $CR^{19}$;
$A^8$ is N or $CR^{20}$;
$R^{17}$, $R^{18}$, $R^{19}$ and $R^{20}$, which may be the same or different, are each hydrogen, alkyl$_{C1-10}$, alkene$_{C2-12}$, aryl, aralkyl, halogen, trifluoroalkyl, cyano, nitro, —NR$^d$R$^e$, —OR$^d$, glycol, —C(O)R$^d$, —C(O)OR$^d$, —OC(O)R$^d$, —S(O)R$^d$R$^e$, —C(O)NR$^d$R$^e$ or a solubilising group;
$R^{16}$ is —CR$^{21}$═CR$^{22}$Y, —C≡C—R$^{23}$ or together with $R^{18}$ forms a ring IV:

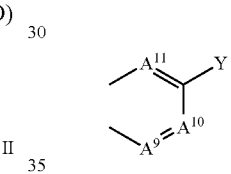

$A^9$ is N or $CR^{24}$;
$A^{10}$ is N or $CR^{25}$;
$A^{11}$ is N or $CR^{26}$;
$R^{23}$ is a group V:

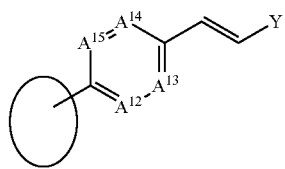

in which
$A^{12}$ is N or $CR^{27}$;
$A^{13}$ is N or $CR^{28}$;
$A^{14}$ is N or $CR^{29}$;
$A^{15}$ is N or $CR^{30}$;
$R^{21}$ and $R^{22}$, which may be the same or different, are each hydrogen, alkyl$_{C1-10}$, alkene$_{C2-12}$, aryl, halogen or trifluoroalkyl;
$R^{24}$, $R^{25}$, $R^{26}$, $R^{27}$, $R^{28}$, $R^{29}$ and $R^{30}$, which may be the same or different, are each hydrogen, alkyl$_{C1-10}$, alkene$_{C2-12}$, aryl, halogen, trifluoroalkyl, —OR$^f$, glycol or a solubilising group;
$R^d$, $R^e$ and $R^f$, which may be the same or different, are each hydrogen or alkyl$_{C1-10}$;
Y is —CO$_2$R$^{31}$, —COH, —CO$_2$CH$_2$C≡CH, —CN, —SF$_5$, —SO$_3$H, —SO$_2$NH$_2$, —SO$_2$CF$_3$, —CF$_3$, —CO$_2$(CH$_2$)$_m$SH, —CO$_2$(CH$_2$)$_m$SO$_2$F, —CO$_2$(CH$_2$)$_m$CH═CH$_2$, —C=NR$^{32}$ or —C=N$^+$R$^{33}$R$^{34}$; R$^{31}$ is hydrogen, alkyl$_{C1-10}$, alkene$_{C2-12}$, aryl or a photocleavable group, such as —CH$_2$aryl-NO$_2$;

R$^{32}$, R$^{33}$ and R$^{34}$, which may be the same or different, are each hydrogen, alkyl$_{C1-10}$, alkene$_{C2-12}$ or aryl;

m is an integer from 1 to 9;

and isomers thereof;

in free or in salt form.

As used herein, the term "alkyl" refers to a fully saturated, branched, unbranched or cyclic hydrocarbon moiety, i.e. primary, secondary or tertiary alkyl or, where appropriate, cycloalkyl or alkyl substituted by cycloalkyl, they may also be saturated or unsaturated alkyl groups. Where not otherwise identified, preferably the alkyl comprises 1 to 10 carbon atoms, more preferably 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein the term "aryl" refers to an aromatic monocyclic or multicyclic hydrocarbon ring system consisting only of hydrogen and carbon and containing from 6 to 19 carbon atoms, preferably 6 to 10 carbon atoms, where the ring system may be partially saturated. Aryl groups include, but are not limited to groups such as fluorenyl, phenyl, indenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, alkynyl, halo, haloalkyl, cyano, nitro, amino, amidine, aryl, aralkyl, cycloalkyl, cycloalkylalkyl, heterocyclyl, heterocyclylalkyl, heteroaryl or heteroarylalkyl. Preferred aryl groups are optionally substituted phenyl or naphthyl groups.

An aryl group may be mono-, bi-, tri-, or polycyclic, preferably mono-, bi-, or tricyclic, more preferably mono- or bicyclic.

As used herein, the term "heteroaryl" refers to a 5-14 membered monocyclic- or bicyclic- or polycyclic-aromatic ring system, having 1 to 8 heteroatoms selected from N, O or S. Preferably, the heteroaryl is a 5-10 or 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinolinyl, 1-, 3-, 4-, 5-, 6-, 7-, or 8-isoquinolinyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido [2,3-d]-o-oxazinyl, 1-, 3-, or 5-1H-pyrazolo[4,3-d]-oxazolyl, 2-, 4-, or 54H-imidazo[4,5-d] thiazolyl, 3-, 5-, or 8-pyrazino[2,3-d]pyridazinyl, 2-, 3-, 5-, or 6-imidazo[2,1-b] thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b] thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, 7-benzofuranyl, 2-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

A heteroaryl group may be mono-, bi-, tri-, or polycyclic, preferably mono-, bi-, or tricyclic, more preferably mono- or bicyclic.

A heteroaryl group may optionally be substituted by aryl or aralkyl, e.g. benzyl.

In one aspect of the invention there is provided a highly conjugated retinoid compound of formula I:

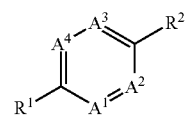

I wherein A$^1$ is CR$^3$, A$^2$ is CR$^4$, A$^3$ is CR$^5$ and A$^4$ is CR$^6$; and R$^1$, R$^2$, R$^3$, R$^4$, R$^5$ and R$^6$ are each as herein defined.

In one aspect of the invention there is provided a highly conjugated retinoid compound of formula I:

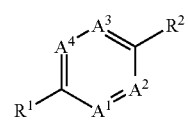

I wherein A$^1$, A$^2$, A$^3$, A$^4$ and R$^2$ are each as herein defined; and

R$^1$ together with R$^6$ forms a ring II:

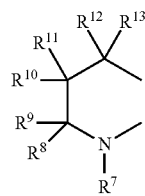

II wherein $R^7$, $R^8$, $R^9$, $R^{10}$, $R^{11}$, $R^{12}$ and $R^{13}$ are each as herein defined.

Preferably in this aspect of the invention wherein $A^1$ is $CR^3$, $A^2$ is $CR^4$, $A^3$ is $CR^5$ and $A^4$ is $CR^6$.

In one aspect of the invention there is provided a highly conjugated retinoid compound of formula I as herein defined wherein $R^2$ is a group III:

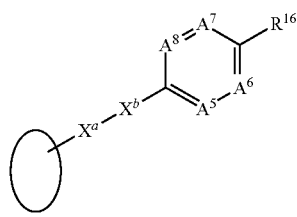

III wherein $X^a$ is —C≡C— and $X^b$ is —C≡C—; and
$A^5$, $A^6$, $A^7$, $A^8$ and $R^{16}$ are each as herein defined.

In one aspect of the invention there is provided a highly conjugated retinoid compound of formula I as herein defined wherein $R^2$ is a group III wherein $X^a$ is —C≡C— and $X^b$ is absent.

In one aspect of the invention there is provided a highly conjugated retinoid compound of formula I as herein defined wherein $R^2$ is a group III wherein $X^a$ is —CH=CH— and $X^b$ is absent.

In one aspect of the invention there is provided a highly conjugated retinoid compound of formula I as herein defined wherein $R^2$ is a group III wherein $X^a$ is —N=CH— and $X^b$ is absent.

In one aspect of the invention there is provided a highly conjugated retinoid compound of formula I as herein defined wherein $R^2$ is a group III;

wherein $A^5$ is $CR^{17}$, $A^6$ is $CR^{18}$, $A^7$ is $CR^{19}$ and $A^8$ is $CR^{20}$; and $X^a$, $X^b$, $R^{16}$, $R^{17}$, $R^{18}$, $R^{19}$ and $R^{20}$ are each as herein defined.

In one aspect of the invention there is provided a highly conjugated retinoid compound of formula I as herein defined wherein $R^2$ is a group III;

wherein $A^5$ is $CR^{17}$, $A^6$ is $CR^{18}$, $A^7$ is $CR^{19}$ and $A^8$ is $CR^{20}$; and $R^{17}$, $R^{19}$ and $R^{20}$ are each as herein defined;

$R^{16}$ together with $R^{18}$ forms a ring IV:

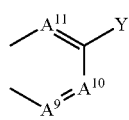

IV wherein $A^9$, $A^{10}$, $A^{11}$ and Y are each as herein defined.

In one aspect of the invention there is provided a highly conjugated retinoid compound of formula I as herein defined wherein $R^2$ is a group III;

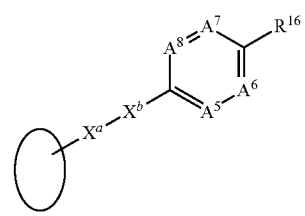

III and $R^{16}$ is —C≡C—$R^{23}$
wherein $R^{23}$ is a group V:

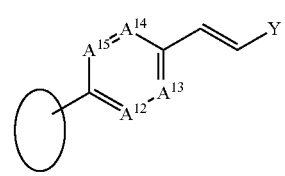

V in which
$A^{12}$ is $CR^{27}$, A is $CR^{27}$, $A^{13}$ is $CR^{28}$, $A^{14}$ is $CR^{29}$ and $A^{15}$ is $CR^{30}$; and $R^{27}$, $R^{28}$, $R^{29}$, $R^{30}$ and Y are each as herein defined.

In one aspect of the invention there is provided a highly conjugated retinoid compound of formula I as herein defined wherein $R^2$ is a group III;

and $R^{16}$ is —C≡C—$R^{23}$, $R^{23}$ is a group V and Y is —$CO_2R^{31}$, —COH, —$CO_2CH_2$C≡CH, —CN, —$SF_5$, —$SO_3H$, —$SO_2NH_2$, —$SO_2CF_3$, in which $R^{31}$ is as herein defined. Preferably Y is —$CO_2R^{31}$ in which $R^{31}$ is as herein defined. Preferably $R^{31}$ is hydrogen or $alkyl_{C1-10}$.

In one aspect of the invention $R^7$ or $R^{7a}$ is alkyl C1-10, preferably alkyl C1-3.

In one aspect of the invention $R^7$ is propynyl, —$(CH_2)_n$C≡CH, —$(CH_2)_n$SH, —$(CH_2)_n SO_2F$ or —$(CH_2)_n$C=$CH_2$; in which n is as herein defined.

In one aspect of the invention $R^8$, $R^9$, $R^{10}$ and $R^{11}$ are each hydrogen.

In one aspect of the invention one pair of $R^8$ and $R^{10}$ or $R^9$ and $R^{11}$ represent a bond.

In one aspect of the invention $R^{12}$ and $R^{13}$ are the same or different; $R^{12}$ and $R^{13}$ may each represent alkyl C1-4, e.g. methyl.

As used herein, the term "halogen" or "halo" refers to fluoro, chloro, bromo, and iodo.

In one aspect of the invention $R^2$ is a group VI:

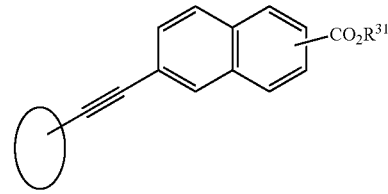

VI wherein $R^{31}$ is as herein defined.

In another aspect of the invention R² is a group VII:

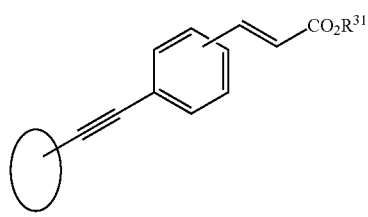

wherein R³¹ is as herein defined.

In another aspect of the invention R² is a group VIII:

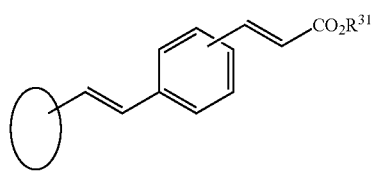

wherein R³¹ is as herein defined.

In another aspect of the invention R² is a group IX:

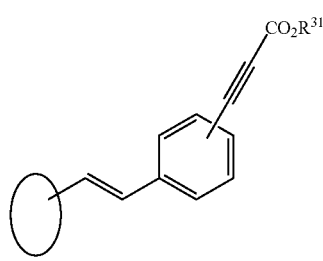

wherein R³¹ is as herein defined.

The moiety —CO₂R³¹ is preferably in the 4-position, i.e. in the para position to the ethynyl group. Preferably R³¹ is hydrogen.

According to one aspect of the invention there is provided a highly conjugated retinoid compound of formula IIa:

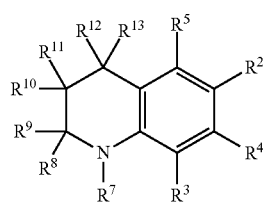

in which R³, R⁴, R⁵, R⁷, R⁸, R⁹, R¹⁰, R¹¹, R¹², R¹³ are each as herein defined; and R² is a group VI, VII, VIII or IX as herein defined and isomers thereof;

in free or in salt form.

Illustrative compounds of formula I which may be mentioned include those selected from the group consisting of:

(2E)-3-(4-2-[4,4-Dimethyl-1-(propan-2-yl)-1,2,3,4-tetrahydroquinolin-6-yl]ethynylphenyl)prop-2-enoic acid (DC324);

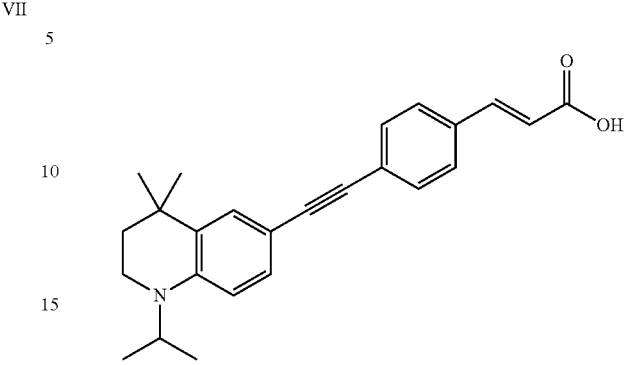

(2E)-3-(4-2-[4,4-dimethyl-1-(propyn-2-yl)-1,2,3,4-tetrahydroquinolin-6-yl]ethynylphenyl)prop-2-enoic acid (DC474); and

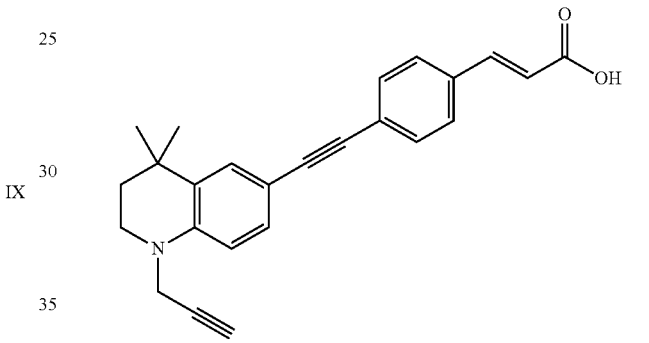

(2E)-3-(4-2-[4,4-dimethyl-1-(propyn-2-yl)-1,2,3,4-tetrahydroquinolin-6-yl]ethynylphenyl)prop-2-enoic acid methyl ester (DC473);

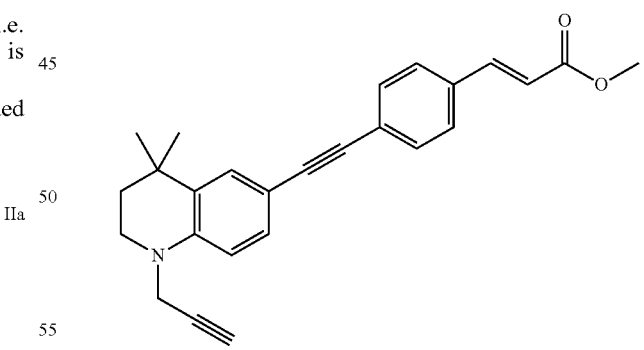

and isomers thereof;

in free or in salt form.

Compounds of formula I are either known per se or may be prepared by methods described in International Patent application No. WO 2016/055800.

Excitation of the fluorescent compound to a short-lived excited singlet state occurs upon treatment with light, this light is then emitted as fluorescence when the compound resumes singlet ground state energy. Alternatively, the excited singlet state may instead transfer this energy, via intersystem crossing, to an excited triplet state. The compound in an excited triplet state can be quenched by a nearby entity, in order to give another compound which is no longer fluorescent, leading to a gradual dimming. It is possible that the compounds of the present invention are entering a stable excited triplet state which is susceptible to quenching via a type-I or -II reaction.

In a type-I reaction, the excited triplet state can participate in electron-transfer to a biological substrate, leading to the formation of radicals and radical ions. After interaction with oxygen, these radicals can produce oxygenated products such as superoxide ions, $O_2^-$. Type-11 reactions generate the short-lived and highly reactive cytotoxic agent, singlet oxygen ($^1O_2$), by conversion from stable triplet oxygen ($^3O_2$).

Singlet oxygen is much more reactive than triplet oxygen, due to the spin inversion of one of its outer electrons. Rather than two partially filled outer antibonding orbitals each containing one electron of the same spin, $(\sigma_{2p})^2(\pi_{2px})^2(\pi_{2py})^2(\pi_{2px*})^1(\pi_{2py*})^1$, as is found in triplet oxygen, singlet oxygen has one filled outer antibonding orbital with the electrons in opposite spin, $(\sigma_{2p})^2(\pi_{2px})^2(\pi_{2py})^2(\pi_{2px*})^2$.

FIG. 1 herein provides a Jablonski diagram showing the formation of singlet oxygen. In FIG. 1 PS denotes a photosensitizer in a ground singlet state. Light energy transforms this in to an excited singlet state, denoted by $^1PS*$. Excited singlet states are short lived. They can either release light energy as fluorescence to return to a singlet ground state, or form an excited triplet state, denoted by $^3PS*$. Energy transfer can occur from the excited triplet state to form singlet oxygen.[3]

Human cells are biologically responsive to singlet oxygen production; UVA radiation induces singlet oxygen in cells, which acts as the effector for a signal transduction pathway dependent on the activation of transcription factor AP-2, a factor also activated by ATRA. This leads to the expression of intercellular adhesion molecule-1 (ICAM-1) in human epidermal keratinocytes, a protein normally expressed in inflammatory skin diseases.[4]

FIG. 2 herein illustrates the biological effects of ROS generation. Fluorescent compounds excited by light can lose energy in the form of heat or fluorescence. They can also undergo inter-system crossing and transition into the triplet state. If the triplet state is long lived it can generate reactive oxygen species. At higher concentrations ROS can lead to cell death via necrosis or apoptosis.[5] Notably, in contrast, at low concentrations, ROS is known to cause cell proliferation.

Irradiation of cells with UV can induce an ROS mediated apoptotic response, see FIG. 2. However, it has also been proven to have an effect on the retinoid signalling pathway. UV irradiation of human epidermis in vivo can reduce the expression of RARγ and RXRα at both the mRNA and protein levels. This leads to a loss of retinoid responsive gene expression in the skin.[6] ATRA was found not to enhance UVB-induced apoptosis, according to a study by Lee et al. Although UVB radiation was shown to cause significant apoptosis, there was little difference between the ATRA treated cells and untreated control.[2]

Reactive Oxygen Species (ROS) include hydroxyl (.OH), alkoxyl (RO.) or peroxyl (ROO.), superoxide (O.$_2$) or nitroxyl radicals (NO.), in addition to the non-radicals hydrogen peroxide ($H_2O_2$), organic hydroperoxides (ROOH) and hypochlorous acid (HOCl). ROS are generated as part of the inflammatory response, and are part of the body's natural defence against microbes, owing to their destructive effect on both proteins and DNA. Under normal conditions, the body's cells are protected against ROS by antioxidants, such as reduced glutathione, catalase, and superoxide dismutase. In addition to their role as destructive agents, ROS also play a part as chemical messengers, involved in receptor-mediated signalling pathways and transcriptional activation. ROS are known to be involved in the induction of apoptosis, with mitochondria being both the source and the target of ROS. Oxidation of the mitochondrial pores by ROS may disrupt the mitochondrial membrane potential contributing to cytochrome c release.[7]

The light activated compounds of the present invention are especially suitable for the manufacture of a medicament for use in photodynamic therapy (PDT).

Thus, according to a further aspect of the invention there is provided the use of a highly conjugated retinoid compound in the manufacture of a medicament for use in photodynamic therapy (PDT).

According to a yet further aspect of the invention there is provided a method of treating a patient with photodynamic therapy (PDT), the method comprising the administration of a highly conjugated retinoid compound that generates reactive oxygen species when said compound is activated by light.

The compounds of the invention are biologically inert in the unactivated state, but short pulses of low to medium energy short-wavelength visible light cause defined biological effects. Cells demonstrate a graded response based on the quantity of energy delivered; the lowest energy light induces cells to proliferate in wound healing assays, low to medium-low energy induces cell apoptosis in labelled cells including distinctive membrane blebbing visible within the first 10 minutes following light exposure, and the medium to high energy causes cells to die immediately by necrosis. Importantly, adjacent cells, not exposed to light are unharmed. Proof of concept experiments have been performed in mammalian cells; however, the ability to generate ROS is not species specific and thus at high concentrations should be effective in killing any ROS sensitive cells, including animal, plant, bacterial and fungal cells.

Thus, according to this aspect of the invention the photodynamic therapy (PDT) may comprise non-surgical cell ablation for the treatment of one or more of cancer; the treatment of benign growths; the treatment of immune mediated inflammatory disorders; or the treatment of a disease caused by a pathogenic organism as herein described.

Photodynamic therapy (PDT) can be an effective anticancer treatment option. PDT involves the administration of a tumour-localising photosensitizer (PS) followed by light activation to generate highly cytotoxic reactive oxygen species (ROS), particularly singlet oxygen, which trigger cell apoptosis and necrosis. By localizing both the PS and the light exposure to tumour regions, PDT can selectively kill tumour cells while preserving local tissues. PDT has been used to treat patients with many different types of cancer, including head and neck tumours, breast cancer, gynaecological tumours, brain tumours, colorectal cancer, mesothelioma, and pancreatic cancer. The use of PDT for treating cancers in the head and neck is particularly advantageous over traditional treatment modalities, e.g., surgery and irradiation, as PDT causes less destruction of surrounding tissues and reduces aesthetic and functional impairments. The compounds of the present invention can be used to produce high levels of ROS for the destruction of diseased tissues, such as cancerous tumours.

Thus, according to one aspect of the invention, the photodynamic therapy (PDT) may comprise the treatment of one or more cancer selected from the group wherein the cancer cells are selected from one or more of primary cancer, breast cancer, colon cancer, prostate cancer, non-small cell lung cancer, neuroblastoma, glioblastoma, lymphoma, mesothelioma, liver cancer, intrahepatic bile duct cancer, oesophageal cancer, pancreatic cancer, stomach cancer, laryngeal cancer, brain cancer, ovarian cancer, testicular cancer, cervical cancer, oral cancer, pharyngeal cancer, renal cancer, thyroid cancer, uterine cancer, urinary bladder cancer, hepatocellular carcinoma, thyroid carcinoma, osteosarcoma, small cell lung cancer, leukaemia, myeloma, gastric carcinoma, melanoma, and metastatic cancers. The compounds of the present invention are suitable for a photodynamic therapy (PDT) that causes the apoptosis of cancer cells.

According to a further aspect of the invention the photodynamic therapy (PDT) may comprise the treatment of benign growths e.g. prostatic hyperplasia, keloids or intestinal polyps.

According to a further aspect of the invention the photodynamic therapy (PDT) may comprise the treatment of an immune mediated inflammatory disease in a mammal, e.g. a human, caused by an aberrant immune response. This may include skin (e.g. psoriasis), joint (e.g. rheumatoid arthritis), intestines (inflammatory bowel diseases) and other localised and systemic autoimmune diseases; inflammation driven disease pathologies including graft versus host disease (GVHD) and tissue specific vasculitis.

According to a further aspect of the invention the photodynamic therapy (PDT) may comprise the treatment of a disease in a mammal, e.g. a human, caused by a pathogenic organism. The pathogenic organism may be one which comprises eukaryotic cells or prokaryotic cells. Such pathogenic organisms include but shall not be limited to, bacteria, viruses, fungi, parasites, protozoa, and toxins as well as cells and tissues infected or infiltrated therewith.

One objective of the present invention is to provide a photodynamic method for inactivation/reduction of bacteria (both Gram-positive and Gram-negative) in complex environment like blood, serum and saliva. A further object is to provide a therapy suitable for the treatment of an infectious disease, caused by a pathogenic organism, including but not limited to bacteria, viruses, fungi, parasites, protozoa, and toxins.

Concentrations of photosensitizer used in the study were as follows: 100 µM, 10 µM, 1 µM, 0.1 µM and 0.01 µM.

At low concentrations the compounds of the present invention can deliver low dose ROS, which can be used to initiate tissue recovery and regeneration through cellular proliferation. Therefore, according a further aspect of the present invention there is provided a method of treating a patient with photodynamic therapy (PDT), the method comprising the administration of a highly conjugated retinoid compound that generates reactive oxygen species when said compound is activated by light to initiate tissue recovery and/or regeneration.

According to a yet further aspect of the invention chaperones may be covalently bound to the compounds described herein. Such covalently linked compound-chaperones can be used for selective targeting of a specific subset of cells. Suitable chaperones include pharmaceutical compounds or biologics, such as, antibodies, e.g. antibodies to cell surface proteins, cytokines, chemokines, hormones and growth factors (e.g. EGF) that bind to cellular receptors; affimers and other selective binding agents, or other transport systems, such as transport proteins, polyglycosides or drug delivery systems, including cyclodextrins etc.

The chaperones may be coupled to the compounds described herein covalently, for example, by ester or amide linkages. The technique of "click" chemistry, i.e. joining substrates to biomolecules may suitably be used in the preparation of the compound-chaperones of the present invention. One example of a linkage for coupling a compound of the invention with a chaperone as herein described is a triazolo linkage (see Example 3 herein) which can be attached to the chaperone.

Such compound-chaperones are novel per se. Therefore, according to a further aspect of the invention there is provided a compound-chaperone comprising a highly conjugated retinoid as herein described covalently linked to a chaperone entity as herein described.

More specifically, the present invention provides a compound-chaperone comprising a compound of formula I as herein defined covalently linked to a chaperone entity.

According to this aspect of the invention there is especially provided a compound-chaperone wherein the chaperone is a biologic as herein defined.

The invention further provides the use of a compound-chaperone in the generation of reactive oxygen species when said compound is activated by light.

As described herein, the compounds of the invention are biologically inert in the unactivated state. Furthermore, the compounds of the invention, including the compound-chaperone entities described herein are advantageous in that they are, inter alia, bioavailable, or more bioavailable than conventionally known compounds used in photodynamic therapy. In addition, conventionally known compounds used in photodynamic therapy comprise an organometallic agent. Thus, the compounds described herein including the compound-chaperone entities are also advantageous in that they are, inter alia, non-metallic and are generally less toxic than known compounds used in photodynamic therapy.

In addition, the invention provides a method of treating a patient with photodynamic therapy (PDT), the method comprising the administration of a compound-chaperone that generates reactive oxygen species when said compound is activated by light.

Furthermore, certain of the compounds of formula I are also novel per se. Thus, according to this aspect of the invention there is provided a highly conjugated retinoid compound is a compound of formula I:

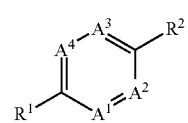

in which $A^1$ is N or $CR^3$;

$A^2$ is N or $CR^4$;

$A^3$ is N or $CR^5$;

$A^4$ is N or $CR^6$;

$R^3$, $R^4$, $R^5$ and $R^6$, which may be the same or different, are each hydrogen, alkyl$_{C1-10}$, alkene$_{C2-12}$, aryl, aralkyl, halogen, trifluoroalkyl, cyano, nitro, —NR$^a$R$^b$, —OR$^a$, glycol, —C(O)R$^a$, —C(O)OR$^a$, —OC(O)R$^a$, —S(O)R$^a$R$^b$, —C(O)NR$^a$R$^b$ or a solubilising group;

$R^1$ is —$NR^{7a}R^{7b}$ or together with $R^6$ forms a ring II:

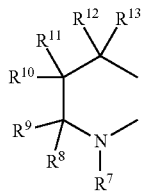

$R^7$ and $R^{7a}$ are each hydrogen, propynyl, —$(CH_2)_nC\equiv CH$, —$(CH_2)_nSH$, —$(CH_2)_nSO_2F$ or —$(CH_2)_nC=CH_2$, alkyl$_{C1-10}$, said alkyl being optionally substituted by aryl or heteroaryl;

$R^{7b}$ is hydrogen, propynyl, alkyl$_{C1-10}$, said alkyl being optionally substituted by aryl or heteroaryl;

$R^8$, $R^9$, $R^{10}$ and $R^{11}$, which may be the same or different, are each hydrogen or alkyl$_{C1-4}$, aryl, halogen, trifluoroalkyl, —$OR^c$ or glycol, or together one pair of $R^8$ and $R^{10}$ or $R^9$ and $R^{11}$ represent a bond;

$R^{12}$ and $R^{13}$, which may be the same or different, are each hydrogen, alkyl$_{C1-4}$ or together one pair of $R^{10}$ and $R^{12}$ or $R^{11}$ and $R^{13}$ represent a bond, or $R^{12}$ and $R^{13}$ together form a group:

=$CR^{14}R^{15}$ provided that the pair of $R^{10}$ and $R^{12}$ or $R^{11}$ and $R^{13}$ does not represent a bond if a pair from $R^8$, $R^9$, $R^{10}$ and $R^{11}$ represents a bond;

$R^{14}$ and $R^{15}$, which may be the same or different, are each hydrogen or alkyl$_{C1-10}$; and $R^a$, $R^b$ and $R^c$, which may be the same or different, are each hydrogen or alkyl$_{C1-10}$;

n is an integer from 1 to 6;

$R^2$ is a group III:

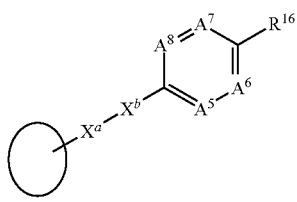

in which $X^a$ is —$C\equiv C$—, —$CH=CH$— or —$N=CH$—;

$X^b$ is —$C\equiv C$— or is absent;

$A^5$ is N or $CR^{17}$;

$A^6$ is N or $CR^{18}$;

$A^7$ is N or $CR^{19}$;

$A^8$ is N or $CR^{20}$;

$R^{17}$, $R^{18}$, $R^{19}$ and $R^{20}$, which may be the same or different, are each hydrogen, alkyl$_{C1-10}$, alkene$_{C2-12}$, aryl, aralkyl, halogen, trifluoroalkyl, cyano, nitro, —$NR^dR^e$, —$OR^d$, glycol, —$C(O)R^d$, —$C(O)OR^d$, —$OC(O)R^d$, —$S(O)R^dR^e$, —$C(O)NR^dR^e$ or a solubilising group;

$R^{16}$ is —$CR^{21}=CR^{22}Y$, —$C\equiv C$—$R^{23}$ or together with $R^{18}$ forms a ring IV:

$A^9$ is N or $CR^{24}$;
$A^{10}$ is N or $CR^{25}$;
$A^{11}$ is N or $CR^{26}$;
$R^{23}$ is a group V:

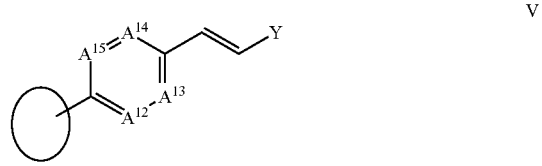

in which
$A^{12}$ is N or $CR^{27}$;
$A^{13}$ is N or $CR^{28}$;
$A^{14}$ is N or $CR^{29}$;
$A^{15}$ is N or $CR^{30}$;

$R^{21}$ and $R^{22}$, which may be the same or different, are each hydrogen, alkyl$_{C1-10}$, alkene$_{C2-12}$, aryl, halogen or trifluoroalkyl;

$R^{24}$, $R^{25}$, $R^{26}$, $R^{27}$, $R^{28}$, $R^{29}$ and $R^{30}$, which may be the same or different, are each hydrogen, alkyl$_{C1-10}$, alkene$_{C2-12}$, aryl, halogen, trifluoroalkyl, —$OR^e$, glycol or a solubilising group;

$R^d$, $R^e$ and $R^f$, which may be the same or different, are each hydrogen or alkyl$_{C1-10}$;

Y is —$CO_2R^{31}$, —COH, —$CO_2CH_2C\equiv CH$, —CN, —$SF_5$, —$SO_3H$, —$SO_2NH_2$, —$SO_2CF_3$, —$CF_3$, —$CO_2(CH_2)_mSH$, —$CO_2(CH_2)_mSO_2F$, —$CO_2(CH_2)_mCH=CH_2$, —$C=NR^{32}$ or —$C=N^+R^{33}R^{34}$; $R^{31}$ is hydrogen, alkyl$_{C1-10}$, alkene$_{C2-12}$, aryl or a photocleavable group, such as —$CH_2aryl-NO_2$;

$R^{32}$, $R^{33}$ and $R^{34}$, which may be the same or different, are each hydrogen, alkyl$_{C1-10}$, alkene$_{C2-12}$ or aryl;

m is an integer from 1 to 9;
and isomers thereof;
in free or in salt form.

In one aspect of the invention there is provided a highly conjugated retinoid compound of formula I as herein described, provided that when $R^7$ is methyl, $R^8$, $R^9$, $R^{10}$ and $R^{11}$ are each hydrogen, $X^a$ is —$C\equiv C$— and $X^b$ is absent, Y is not —$C_2R^{31}$.

In one aspect of the invention there is provided a highly conjugated retinoid compound of formula I:

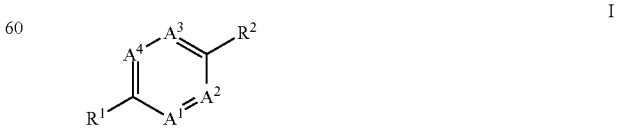

wherein $A^1$ is $CR^3$, $A^2$ is $CR^4$, $A^3$ is $CR^5$ and $A^4$ is $CR^6$; and $R^1$, $R^2$, $R^3$, $R^4$, $R^5$ and $R^6$ are each as herein defined.

In one aspect of the invention there is provided a highly conjugated retinoid compound of formula I:

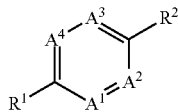

I wherein $A^1$, $A^2$, $A^3$, $A^4$ and $R^2$ are each as herein defined; and
$R^1$ together with $R^6$ forms a ring II:

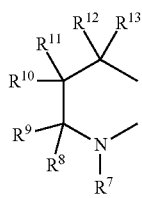

II wherein $R^7$, $R^8$, $R^9$, $R^{10}$, $R^{11}$, $R^{12}$ and $R^{13}$ are each as herein defined.

Preferably in this aspect of the invention wherein $A^1$ is $CR^3$, $A^2$ is $CR^4$, $A^3$ is $CR^5$ and $A^4$ is $CR^6$.

In one aspect of the invention there is provided a highly conjugated retinoid compound of formula I as herein defined wherein $R^2$ is a group III:

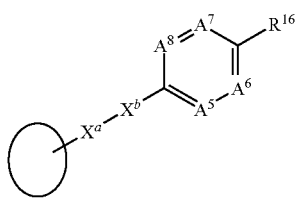

III wherein $X^a$ is —C≡C— and $X^b$ is —C≡C—; and
$A^5$, $A^6$, $A^7$, $A^8$ and $R^{16}$ are each as herein defined.

In one aspect of the invention there is provided a highly conjugated retinoid compound of formula I as herein defined wherein $R^2$ is a group III wherein $X^a$ is —C≡C— and $X^b$ is absent.

In one aspect of the invention there is provided a highly conjugated retinoid compound of formula I as herein defined wherein $R^2$ is a group III wherein $X^a$ is —CH=CH— and $X^b$ is absent.

In one aspect of the invention there is provided a highly conjugated retinoid compound of formula I as herein defined wherein $R^2$ is a group III wherein $X^a$ is —N=CH— and $X^b$ is absent.

In one aspect of the invention there is provided a highly conjugated retinoid compound of formula I as herein defined wherein $R^2$ is a group III;
wherein $A^5$ is $CR^{17}$, $A^6$ is $CR^{18}$, $A^7$ is $CR^{19}$ and $A^8$ is $CR^{20}$; and
$X^a$, $X^b$, $R^{16}$, $R^{17}$, $R^{18}$, $R^{19}$ and $R^{20}$ are each as herein defined.

In one aspect of the invention there is provided a highly conjugated retinoid compound of formula I as herein defined wherein $R^2$ is a group III;

wherein $A^5$ is $CR^{17}$, $A^6$ is $CR^{18}$, $A^7$ is $CR^{19}$ and $A^8$ is $CR^{20}$; and
$R^{17}$, $R^{19}$ and $R^{20}$ are each as herein defined;
$R^{16}$ together with $R^{18}$ forms a ring IV:

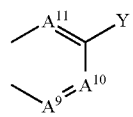

IV wherein $A^9$, $A^{10}$, $A^{11}$ and Y are each as herein defined.

In one aspect of the invention there is provided a highly conjugated retinoid compound of formula I as herein defined wherein $R^2$ is a group III;

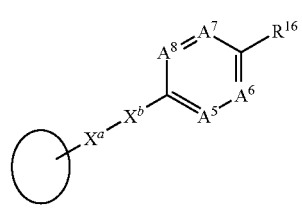

III and $R^{16}$ is —C≡C—$R^{23}$
wherein $R^{23}$ is a group V:

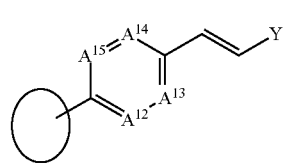

V in which
$A^{12}$ is $CR^{27}$, $A^{13}$ is $CR^{28}$, $A^{14}$ is $CR^{29}$ and $A^{15}$ is $CR^{30}$; and
$R^{27}$, $R^{28}$, $R^{29}$, $R^{30}$ and Y are each as herein defined.

In one aspect of the invention there is provided a highly conjugated retinoid compound of formula I as herein defined wherein $R^2$ is a group III;
and $R^{16}$ is —C≡C—$R^{23}$, $R^{23}$ is a group V and Y is —$CO_2R^{31}$, —COH, —$CO_2CH_2$C≡CH, —CN, —$SF_5$, —$SO_3H$, —$SO_2NH_2$, —$SO_2CF_1$, in which $R^{31}$ is as herein defined. Preferably Y is —$CO_2R^{31}$ in which $R^{31}$ is as herein defined. Preferably $R^{31}$ is hydrogen or alkyl$_{C1-10}$.

In one aspect of the invention $R^7$ or $R^{7a}$ is alkyl C1-10, preferably alkyl C1-3.

In one aspect of the invention $R^8$, $R^9$, $R^{10}$ and $R^{11}$ are each hydrogen.

In one aspect of the invention one pair of $R^8$ and $R^{10}$ or $R^9$ and $R^{11}$ represent a bond.

In one aspect of the invention $R^{12}$ and $R^{13}$ are the same or different; $R^{12}$ and $R^{13}$ may each represent alkyl C1-4, e.g. methyl.

As used herein, the term "halogen" or "halo" refers to fluoro, chloro, bromo, and iodo.

In one aspect of the invention R² is a group VI:

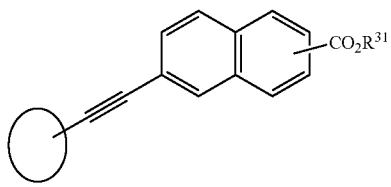

VI wherein R³¹ is as herein defined.

In another aspect of the invention R² is a group VII:

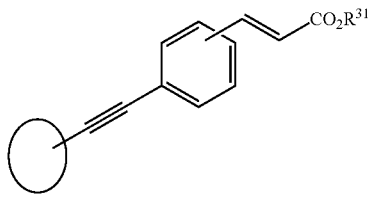

VII wherein R³¹ is as herein defined.

In another aspect of the invention R² is a group VIII:

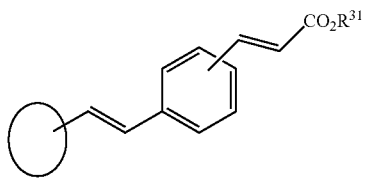

VIII wherein R³¹ is as herein defined.

In another aspect of the invention R² is a group IX:

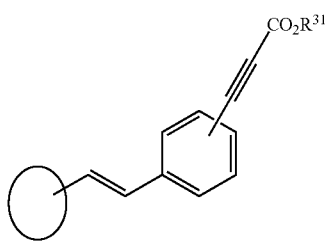

IX wherein R³¹ is as herein defined.

The moiety —CO₂R³¹ is preferably in the 4-position, i.e. in the para position to the ethynyl group. Preferably R³¹ is hydrogen.

Novel compounds which may be specifically mentioned include:
(2E)-3-(4-2-[4,4-Dimethyl-1-(propan-2-yl)-1,2,3,4-tetrahydroquinolin-6-yl]ethynylphenyl)prop-2-enoic acid (DC324);

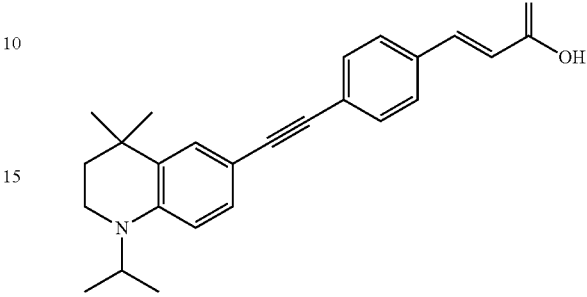

(2E)-3-(4-2-[4,4-dimethyl-1-(propyn-2-yl)-1,2,3,4-tetrahydroquinolin-6-yl]ethynylphenyl)prop-2-enoic acid (DC474); and

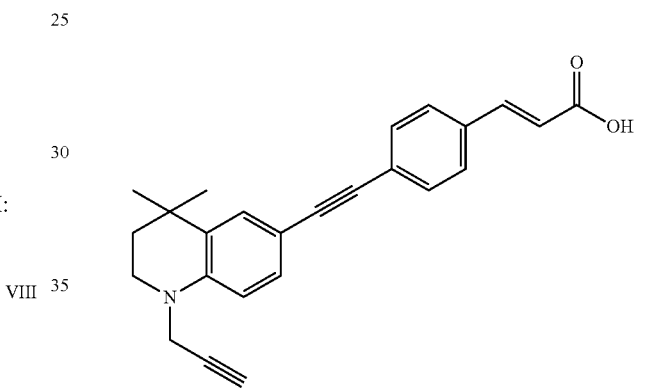

(2E)-3-(4-2-[4,4-dimethyl-1-(propyn-2-yl)-1,2,3,4-tetrahydroquinolin-6-yl]ethynylphenyl)prop-2-enoic acid methyl ester (DC473);

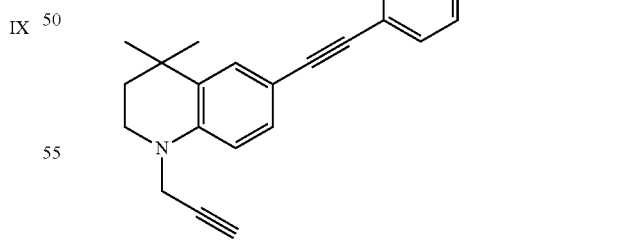

and isomers thereof;
in free or in salt form.

The novel compounds of the invention may be prepared by methods known per se. The novel compounds of formula I may be prepared using methods known to the person skilled in the art or by methods described herein. Examples of such preparations are shown schematically:

Scheme I
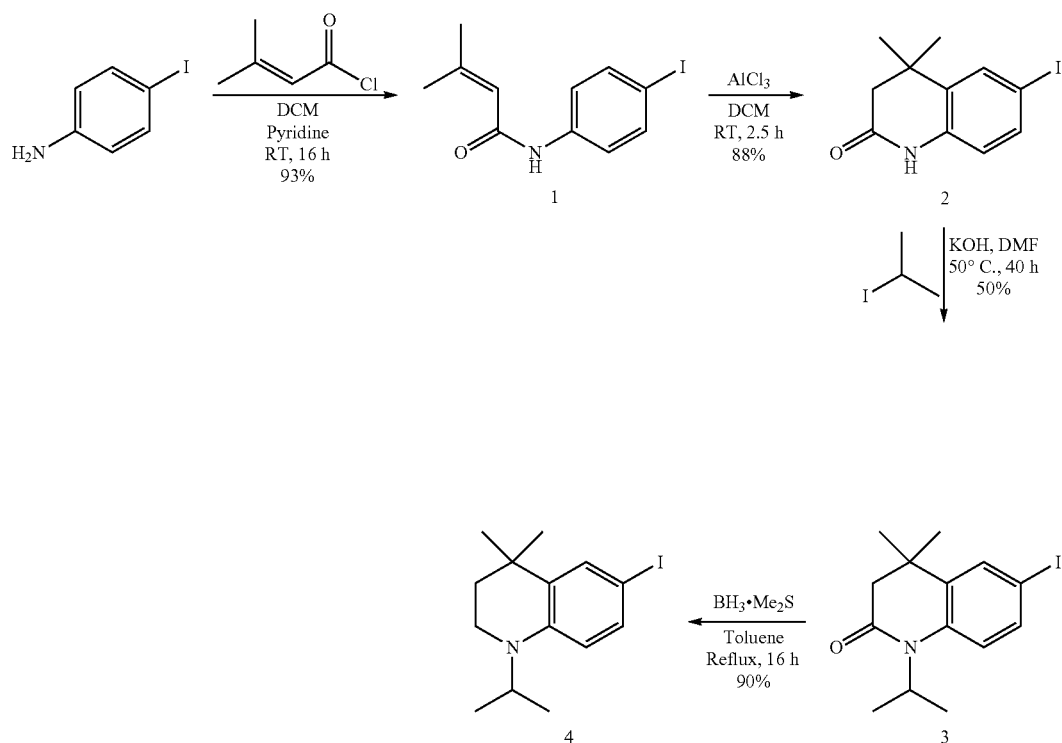
Scheme II
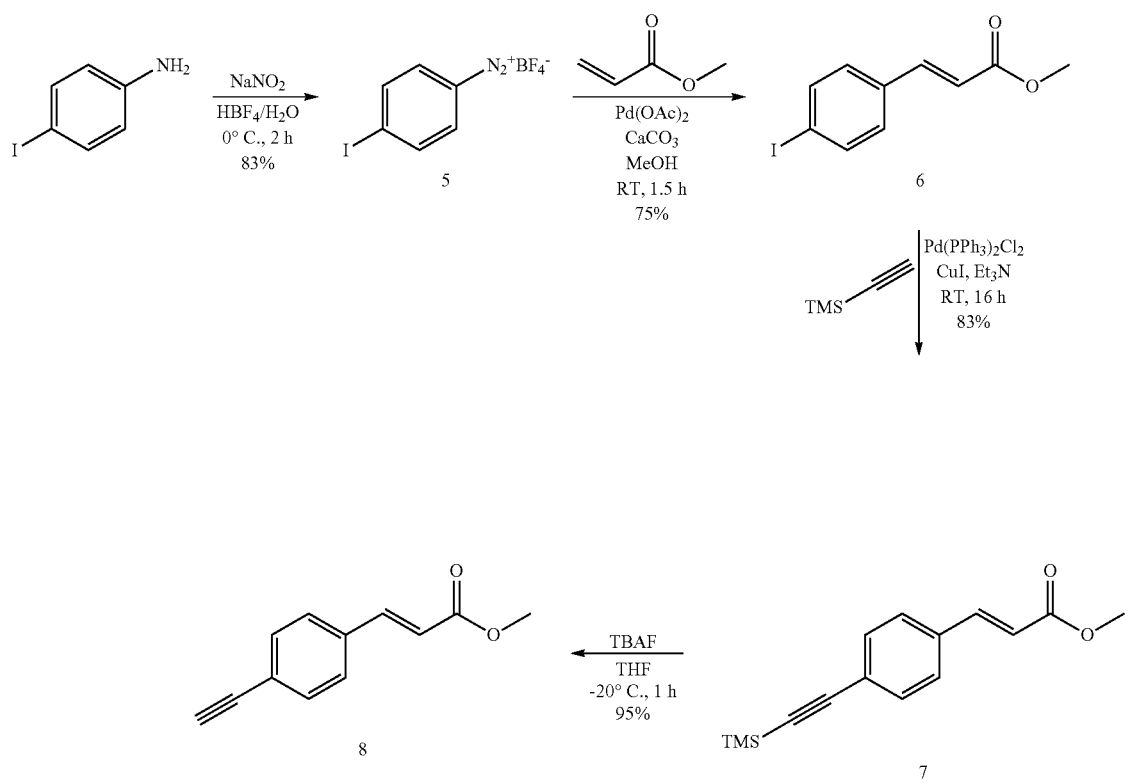

Scheme III
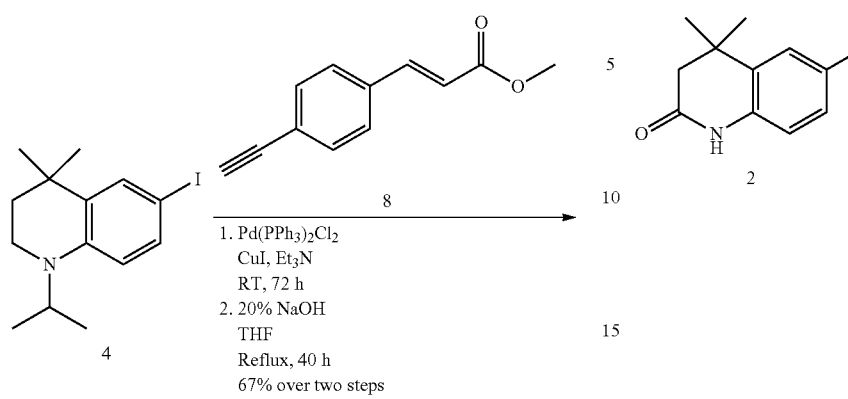
Scheme IV
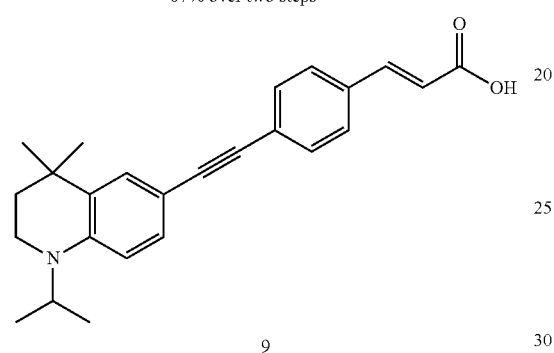
Scheme V
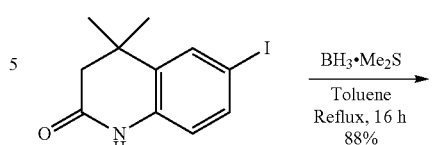
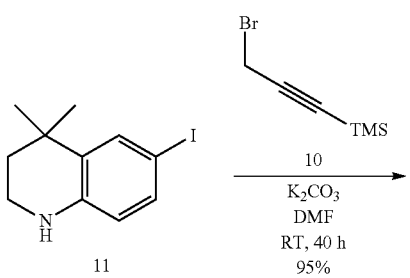
Scheme VI
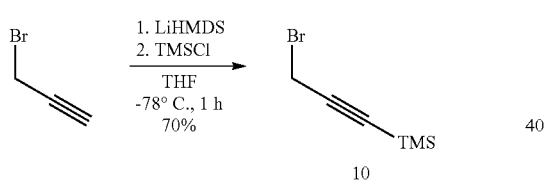
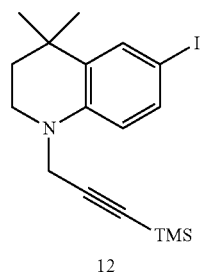
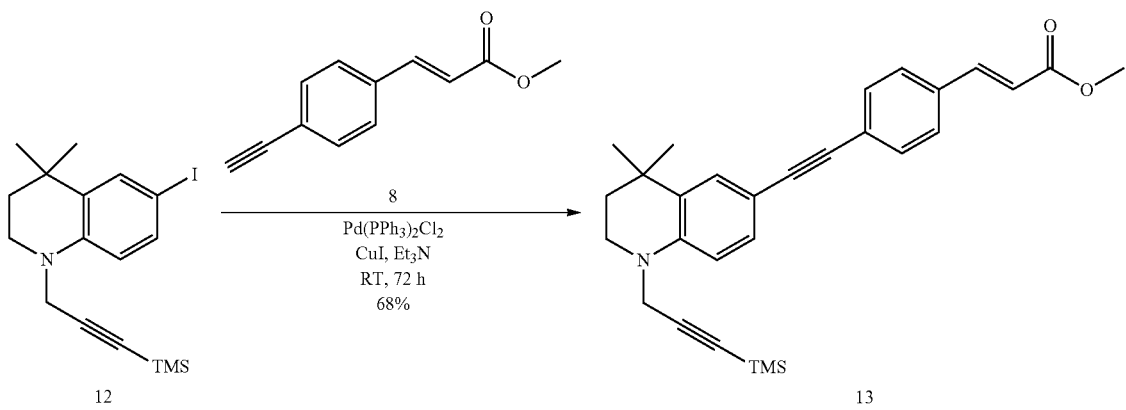
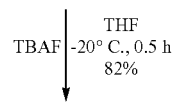

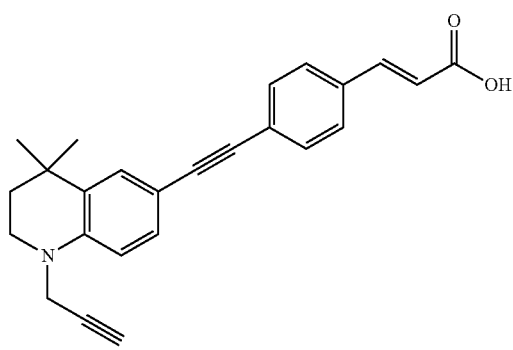 [SMILES: C#CCN1CCC(C)(C)c2cc(C#Cc3ccc(/C=C/C(=O)O)cc3)ccc21]

15

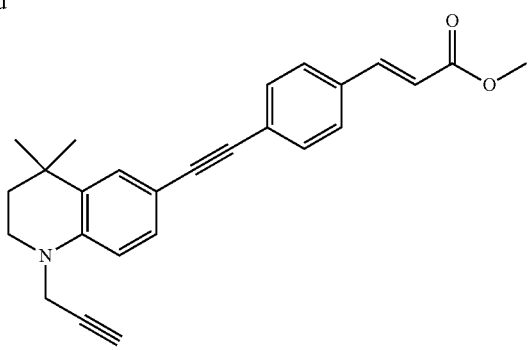

14

Generally, the wavelength suitable for use in the use or the method of the present invention may depend on several factors, such as the depth of the targeted disease site, and the structure or property of the highly conjugated retinoid compound. Thus, the wavelength suitable for activating the highly conjugated retinoid compound may desirably be in the UV spectrum or the blue/violet range of the visible spectrum. More especially the wavelength suitable for activating the highly conjugated retinoid compound may be from about 10 to about 750 nm; preferably from about 100 to about 650 nm; more preferably from about 250 to about 450 nm. The use of a laser diode operating at a wavelength of 405 nm is particularly useful.

According to a further aspect of the present invention there is provided a composition comprising one or more of the compounds of the present invention in combination with one or more pharmaceutically acceptable excipients for use in the generation of reactive oxygen species when said compound is activated by light as herein described.

Thus, according to this aspect of the invention there is provided a composition as herein described for use in the treatment of one or more of cancer; the treatment of benign growths; the treatment of immune mediated inflammatory disorders; or a disease caused by a pathogenic organism as herein described.

The composition of the present invention also includes one or more pharmaceutically acceptable carriers, excipients, adjuvants or diluents. The phrase "pharmaceutically acceptable" is employed herein to refer to those compounds, materials, compositions, and/or dosage forms which are, within the scope of sound medical judgment, suitable for use in contact with the tissues of human beings or, as the case may be, an animal without excessive toxicity, irritation, allergic response, or other problem or complication, commensurate with a reasonable benefit/risk ratio.

The invention further provides a composition as herein described for use in the treatment of one or more of cancer; the treatment of benign growths; the treatment of immune mediated inflammatory disorders; or a disease caused by a pathogenic organism as herein described. The composition of the invention may comprise the compounds described herein or the compound-chaperone entities described herein.

When the composition of the invention is prepared for oral administration, the compounds described above are generally combined with a pharmaceutically acceptable carrier, diluent or excipient to form a pharmaceutical formulation, or unit dosage form.

For oral administration, the composition may be in the form of a powder, a granular formation, a solution, a suspension, an emulsion or in a natural or synthetic polymer or resin for ingestion of the active ingredients from a chewing gum. The composition may also be presented as a bolus, electuary or paste. Orally administered compositions of the invention can also be formulated for sustained release, e.g. the compounds described above can be coated, microencapsulated, or otherwise placed within a sustained delivery device. The total active ingredients in such formulations comprise from 0.1 to 99.9% by weight of the formulation.

Thus, one or more suitable unit dosage forms comprising the compounds of the invention can be administered by a variety of routes including oral, parenteral (including subcutaneous, intravenous, intramuscular and intraperitoneal), rectal, dermal, transdermal, intrathoracic, intrapulmonary, mucosal, intraocular and intranasal (respiratory) routes. The composition may also be formulated in a lipid formulation or for sustained release, for example, using microencapsulation. The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

Pharmaceutical formulations comprising the compounds of the invention can be prepared by procedures known in the art using well-known and readily available ingredients. For example, the compound can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives.

Binding agents can also be included such as carboxymethyl cellulose, hydroxymethylcellulose, hydroxypropyl methylcellulose and other cellulose derivatives, alginates, gelatine, and polyvinylpyrrolidone. Moisturising agents can be included such as glycerol, disintegrating agents such as calcium carbonate and sodium bicarbonate. Agents for retarding dissolution can also be included such as paraffin.

Resorption accelerators such as quaternary ammonium compounds can also be included. Surface active agents such as cetyl alcohol and glycerol monostearate can be included. Adsorptive carriers such as kaolin and bentonite can be added.

Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the compounds of the invention can include buffering agents such as calcium carbonate, magnesium oxide and magnesium carbonate. Suitable buffering agents may also include acetic acid in a salt, citric acid in a salt, boric acid in a salt and phosphoric acid in a salt. Caplets and tablets can also include inactive ingredients such as cellulose, pregelatinised starch, silicon dioxide, hydroxyl propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatine capsules containing at least one compound of the invention can contain inactive ingredients such as gelatine, microcrystalline cellulose, sodium lauryl sulphate, starch, talc, and titanium dioxide, and the like, as well as liquid vehicles such as polyethylene glycols (PEGs) and vegetable oil. Moreover, enteric-coated caplets or tablets containing one or more compounds of the invention are designed to resist disintegration in the stomach and dissolve in the more neutral to alkaline environment of the duodenum.

The therapeutic compounds of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic compounds of the invention can also take the form of an aqueous or anhydrous solution or dispersion, or alternatively the form of an emulsion or suspension or salve.

Thus, the therapeutic compounds may be formulated for parenteral administration (e.g. by injection, for example, bolus injection or continuous infusion) and may be presented in unit dose form in ampules, pre-filled syringes, small volume infusion containers or in multi-dose containers. As noted above, preservatives can be added to help maintain the shelve life of the dosage form. The active compound(s) and other ingredients may form suspensions, solutions, or emulsions in oily or aqueous vehicles, and may contain formulatory agents such as suspending, stabilizing and/or dispersing agents. Alternatively, the active compound(s) and other ingredients may be in powder form, obtained by aseptic isolation of sterile solid or by lyophilisation from solution for constitution with a suitable vehicle, e.g., sterile, pyrogen-free water before use.

It is possible to add, if necessary, an adjuvant chosen from antioxidants, surfactants, other preservatives, film-forming, keratolytic or comedolytic agents, perfumes, flavourings and colourings. Antioxidants such as t-butylhydroquinone, butylated hydroxyanisole, butylated hydroxytoluene and α-tocopherol and its derivatives can be added.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, acetic acid, ethanol, isopropyl alcohol, dimethyl sulphoxide, glycol ethers such as the products sold under the name "Dowanol", polyglycols and polyethylene glycols, C1-C4 alkyl esters of short-chain acids, ethyl or isopropyl lactate, fatty acid triglycerides such as the products marketed under the name "Miglyol", isopropyl myristate, animal, mineral and vegetable oils and polysiloxanes.

Preferably, the composition is in the form of a solvent or diluent comprising one or more of the compounds as described above. Solvents or diluents may include acid solutions, dimethylsulphone, N-(2-mercaptopropionyl) glycine, 2-n-nonyl-1,3-dioxolane and ethyl alcohol. Preferably the solvent/diluent is an acidic solvent, for example, acetic acid, citric acid, boric acid, lactic acid, propionic acid, phosphoric acid, benzoic acid, butyric acid, malic acid, malonic acid, oxalic acid, succinic acid or tartaric acid.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

The solvent may comprise an acetic acid solution. The solvent, for example acetic acid solution, may be present in the composition at a concentration of less than 1%, 0.5%, 0.25%, 0.1%, 0.05% or 0.01% w/w acid, for example acetic acid.

The composition of the present invention may comprise one or more additional therapeutic agents. For instance, where the composition of the present invention is useful in the treatment or prevention of cancer, one or more additional chemotherapeutic and or chemopreventative agents may be included.

When the composition of the present invention is for use in the treatment or prevention of cancer, the one or more additional chemotherapeutic and or chemopreventative agents may be selected from the group consisting of: a chemotherapeutic agent, an immunotherapeutic agent, a gene therapy agent, and a radiotherapeutic agent.

According to this aspect of the invention the composition of the present invention may be administered in combination, separately, simultaneously or sequentially, with a second therapy wherein the second therapy is selected from the group consisting of one or more of a chemotherapeutic agent; an alkylating agent, such as carmustine or temozolomide; a mitotic inhibitor, such as taxanes, (e.g. paclitaxol or docetaxol) or vinca alkaloids (e.g. vinblastine, vincristine, vindestine or vinorelbine); platinum derived compounds (e.g. carboplatin, cisplatin, nedaplatin, oxaliplatin, triplatin tetranitrate or satraplatin); dihydrofolate reductase inhibitors (e.g. aminopterin, methotrexate, pemetrexed or pralatrexate); a DNA polymerase inhibitor (e.g. cytarabine); a ribonucleotide reductase inhibitor (e.g. gemcitabine); a thymidylate synthase inhibitors (e.g. fluorouracil, capecitabine, tegafur, carmofur or floxuridine); aspirin; a non-steroidal anti-inflammatory agent (e.g. ibuprofen); a steroidal anti-inflammatory agent (e.g. a corticosteroid, such as, prednisolone or cortisol); a non-drug oncology therapeutic agent; radiotherapy; tumour embolisation; surgery; and ultrasound.

Where the composition is useful in the treatment of a disease caused by a pathogenic organism, e.g. a bacterial infection and fungal infection; one or more additional antibacterial agents or antifungal agents may be used.

Additionally, the compounds of the present invention are well suited to formulation as sustained release dosage forms and the like. The formulations can be so constituted that they release the active compound, for example, in a particular part of the intestinal or respiratory tract, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g. stents, catheters, peritoneal dialysis tubing, draining devices and the like.

For topical administration, the active agents may be formulated as is known in the art for direct application to a target area. Forms chiefly conditioned for topical application take the form, for example, of creams, milks, gels, powders, dispersion or microemulsions, lotions thickened to a greater or lesser extent, impregnated pads, ointments or sticks, aerosol formulations (e.g. sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic compounds of the invention can be delivered via patches or bandages for dermal administration. Alternatively, the therapeutic compounds can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 μm.

Pharmaceutical formulations for topical administration may comprise, for example, a physiologically acceptable buffered saline solution containing between about 0.001 mg/ml and about 100 mg/ml, for example between 0.1 mg/ml and 10 mg/ml, of one or more of the compounds of the present invention specific for the indication or disease to be treated.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents. The active compounds can also be delivered via iontophoresis. The percentage by weight of a therapeutic agent of the invention present in a topical formulation will depend on various factors, but generally will be from about 0.01% to 95% of the total weight of the formulation, and typically about 0.1-85% by weight.

Drops, such as eye drops or nose drops, may be formulated with one or more of the therapeutic compounds in an aqueous or non-aqueous base also comprising one or more dispersing agents, solubilizing agents or suspending agents. Liquid sprays can be pumped, or are conveniently delivered from pressurized packs. Drops can be delivered via a simple eye dropper-capped bottle, via a plastic bottle adapted to deliver liquid contents drop-wise, or via a specially shaped closure.

The therapeutic compound may further be formulated for topical administration in the mouth or throat. For example, the active ingredients may be formulated as a lozenge further comprising a flavoured base, usually sucrose and acacia or tragacanth; pastilles comprising the composition in an inert base such as gelatine and glycerine or sucrose and acacia; and mouthwashes comprising the composition of the present invention in a suitable liquid carrier.

The compounds of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific infection, indication or disease. Any statistically significant attenuation of one or more symptoms of an infection, indication or disease that has been treated pursuant to the method of the present invention is considered to be a treatment of such infection, indication or disease within the scope of the invention.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g. gelatine or blister packs from which the powder may be administered with the aid of an inhalator, insufflator, or a metered-dose inhaler.

The compounds of the present invention can also be administered in an aqueous solution when administered in an aerosol or inhaled form. Thus, other aerosol pharmaceutical formulations may comprise, for example, a physiologically acceptable buffered saline solution containing between about 0.001 mg/ml and about 100 mg/ml of one or more of the compounds of the present invention specific for the indication or disease to be treated. Dry aerosol in the form of finely divided solid particles of the compounds described above that are not dissolved or suspended in a liquid are also useful in the practice of the present invention. Compounds of the present invention may be formulated as dusting powders and comprise finely divided particles having an average particle size of between about 1 and 5 μm, alternatively between 2 and 3 μm. Finely divided particles may be prepared by pulverization and screen filtration using techniques well-known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating the particular infection, indication or disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic compounds of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

The compounds or compound-chaperones of the present invention may be administered direct to the eye of a patient, e.g. by injection for the treatment or prevention of ocular disorders, such as age-related macular degeneration (AMD). In such treatments the compound or compound-chaperone may be administered to the eye followed by excitation in a photodynamic therapy.

Furthermore, the active ingredients may also be used in combination with other therapeutic agents, for example one or more of pain relievers, anti-inflammatory agents, antihistamines, bronchodilators, chemoprotective agents, chemotherapeutic agents, antibacterial agents and the like.

According to a yet further aspect of the invention there is provided a method of generating a reactive oxygen species which comprises the light activation of a highly conjugated retinoid compound as herein described.

According to an additional aspect of the invention there is provided a process for the manufacture of a compound of formula I as herein described which comprises reacting a compound of formula X;

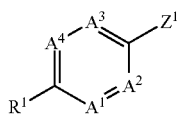

in which $A^1$, $A^2$, $A^3$, $A^4$ and $R^1$ are each as herein defined; and $Z^1$ is a leaving group, for example, halogen, pseudohalogen, boronic acid or boronate ester;

with a compound of formula XI;

$$R^2H \qquad\qquad XI$$

in which $R^2$ is as herein defined.

Alternatively, a process for the manufacture of a compound of formula I as herein described may comprise reacting a compound of formula XII;

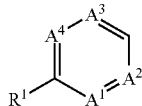

in which $A^1$, $A^2$, $A^3$, $A^4$ and $R^1$ are each as herein defined; with a compound of formula XIII:

$$R^2Z^1 \qquad\qquad XIII$$

in which $Z^1$ is a leaving group, for example, halogen, pseudohalogen, boronic acid or boronate ester.

Compounds of formula XII may be prepared by dealkylation of a compound of formula I in which $R^2$ is alkyl as herein described.

Compounds of formula I may be prepared using methods known to the person skilled in the art or by methods described herein.

The present invention will now be described by way of example only with reference to the accompanying figures in which:

FIG. 1 is a Jablonski diagram showing the formation of singlet oxygen;

FIG. 2 illustrates the biological effects of ROS generation;

FIG. 3 illustrates DC324 localised to one side of the nucleus in large patches of cells;

FIG. 4 illustrates DC324 co-imaged with BODIPY® Golgi stain;

FIG. 5 illustrates that DC324 was the most rapid inducer of cell death;

FIG. 6 illustrates that cell death observations were consistent across different cell lines;

FIG. 7 illustrates that the majority of DMSO treated cells appeared healthy after 47 exposures to 405 nm laser, at 50% strength;

FIG. 8 illustrates that the majority of ATRA treated cells appeared healthy after 47 exposures to 405 nm laser, at 50% strength;

FIG. 9 illustrates that membrane blebbing was induced in DC324 treated cells by 405 nm laser, at 50% strength;

FIG. 10 illustrates DC324 treated cells putatively producing apoptotic bodies;

FIG. 11 illustrates DC324 fluorescence from treated HaCaT cells, imaged with 405 nm laser light, at 50% strength;

FIG. 12 illustrates the dose-dependent response of HaCaT cells treated with DC324 and DC473 and 10 seconds of UV;

FIG. 13 illustrates control treatments stained for superoxide after exposure to UV;

FIG. 14 illustrates active compounds stained for superoxide after exposure to DAPI;

FIG. 15 illustrates inactive DC324 compound treated cells stained for superoxide after UV exposure;

FIG. 16 illustrates DC473 compound treated cells after 2 hours and 24 hours UV exposure;

FIG. 17 illustrates a comparison of DC324 and DC473 compound treated cells;

FIG. 18 illustrates the combined normalised absorbance spectra of DC324, DC473 and DC474 in $CHCl_3$ (10 μM);

FIG. 19 illustrates the combined normalised emission spectra of DC324, DC473 and DC474 in $CHCl_3$ (100 nM) with excitation at their respective maximal absorption wavelengths;

FIG. 20 illustrates the combined normalised absorbance spectra of DC473, DC474 and click-conjugate compound 16 in $CHCl_3$ (10 μM); and FIG. 21 illustrates the combined normalised emission spectra of DC473, DC474, and click-conjugate compound 16 in $CHCl_3$ (100 nM) with excitation at their respective maximal absorption wavelengths.

In the figures, any reference to DC271 is a reference to compound 9 of Example 3 of WO 2016/055800. Reference to DC324 is a reference to compound 9 of Example 1 herein; and reference to DC473 is a reference to compound 14 of Example 2.5 herein; reference to DC474 is a reference to compound 15 of Example 2.6 herein.

The following abbreviations are used in the Examples and other parts of the description:
ATRA: All Trans-Retinoic Acid
DCM: dichloromethane
DMF: N,N-dimethylformamide
DMSO: dimethylsulfoxideEDTA: ethylenediaminetetraacetic acid
EtOAc: ethyl acetate
GCMS: gas chromatography-mass spectrometry
h: hour(s)
KOAc: potassium acetate
RT: room temperature
THF: tetrahydrofuran

GENERAL EXPERIMENTAL

Reagents were purchased from Sigma-Aldrich, Acros Organics, Alfa-Aesar and Fluorochem and used without further purification unless otherwise stated. Solvents were used as supplied, and dried before use with appropriate drying agents if stated. Reactions were monitored in situ by TLC, or NMR spectroscopy. Thin layer chromatography (TLC) was conducted using Merck Millipore silica gel 60G F254 25 glassplates with visualisation by UV lamp. Flash column chromatography was performed using $SiO_2$ from Sigma-Aldrich (230-400 mesh, 40-63 μm, 60 Å) and monitored using TLC. NMR spectra were recorded on Varian VNMRS-700, Varian VNMRS-600, Bruker Avance-400 or Varian Mercury-400 spectrometers operating at ambient probe temperature unless otherwise stated. NMR spectra were recorded in CDCl$_3$ or DMSO-d$_6$ purchased from Goss Scientific. NMR peaks are reported as singlet (s), doublet (d), triplet (t), quartet (q), broad (br), heptet (hept), combinations thereof, or as a multiplet (m). ES-MS was performed by the Durham University departmental service using a TQD (Waters UK) mass spectrometer and Acquity UPLC (Waters Ltd, UK), and accurate mass measurements were obtained using a QTOF Premier mass spectrometer and an Acquity UPLC (Waters Ltd, UK). GCMS was performed by the Durham University departmental service using a Shimadzu QP2010-Ultra. IR spectra were recorded on a Perkin Elmer FT-IR spectrometer. Melting points were obtained using a Gallenkamp melting point apparatus. Elemental analyses were obtained by the Durham University departmental service using an Exeter Analytical CE-440 analyzer.

Synthetic Procedures

Example 1

(2E)-3-(4-2-[4,4-Dimethyl-1-(propan-2-yl)-1,2,3,4-tetrahydroquinolin-6-yl]ethynylphenyl)prop-2-enoic Acid (9)

1.1 N-(4-Iodophenyl)-3-methylbut-2-enamide (1)

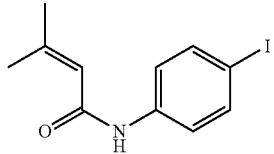

To a solution of 4-iodoaniline (25.0 g, 114.0 mmol) in DCM (400 mL) was added 3,3-dimethylacryloyl chloride (13.36 mL, 120.0 mmol) and the resultant white suspension was stirred for 0.5 h, after which pyridine (9.70 mL, 120 mmol) was added and the solution stirred at RT for 16 h. The solution was diluted with DCM and H$_2$O, washed with sat. NH$_4$Cl, H$_2$O and brine, dried (MgSO$_4$) and evaporated to give a crude light brown solid (33 g) which was recrystallised from EtOH to give compound 1 as a white crystalline solid (31.8 g, 93%): m.p.=136-138° C.; $^1$H NMR (700 MHz, CDCl$_3$) δ 1.91 (s, 3H), 2.22 (s, 3H), 5.68 (s, 1H), 7.01 (s, 1H), 7.33 (m, 2H), 7.60 (d, J=8.8 Hz, 2H); $^{13}$C NMR (101 MHz, CDCl$_3$) δ 20.2, 27.6, 87.2, 118.7, 122.0, 137.8, 138.2, 154.1, 165.5; IR (neat) ν$_{max}$/cm$^{-1}$ 3294 m, 3094, 2964 w, 2890 w, 1666 m, 1586 m, 1430 m, 821 s, 650 m; MS (ES): m/z=302.0 [M+H]$^+$; HRMS (ES) calcd. for C$_{11}$H$_{13}$NOI [M+H]$^+$: 302.0042, found: 302.0050. Found: C, 43.87; H, 4.02; N, 4.64. Calc. for C$_{11}$H$_{12}$NOI: C, 43.88; H, 4.02; N, 4.65%.

1.2 6-Iodo-4,4-dimethyl-1,2,3,4-tetrahydroquinolin-2-one (2)

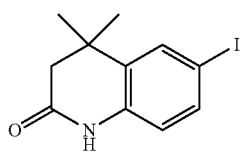

Compound 1 (11.5 g, 38.3 mmol) and AlCl$_3$ (7.66 g, 57.5 mmol) were added to anhydrous DCM (150 mL) under Ar and the resultant solution stirred vigorously for 2.5 h at RT. The reaction was cooled to 0° C., quenched slowly with H$_2$O, diluted with DCM, stirred with 5% NaOH (w/v) until the solution turned off-white, then further washed with H$_2$O and brine, dried (MgSO$_4$) and evaporated to give a crude yellow solid (12.0 g). This was recrystallised from EtOH to give compound 2 as a white crystalline solid (10.2 g, 88%): m.p.=199-202 OC; $^1$H NMR (700 MHz, CDCl$_3$) δ 1.32 (s, 6H), 2.47 (s, 2H), 6.62 (d, J=8.3 Hz, 1H), 7.47 (dd, J=8.3, 1.9 Hz, 1H), 7.56 (d, J=1.8 Hz, 1H), 9.20 (s, 1H); $^{13}$C NMR (176 MHz, CDCl$_3$) δ 27.7, 34.2, 45.2, 86.8, 118.1, 133.7, 135.1, 135.9, 136.6, 171.3; IR (neat) ν$_{max}$/cm$^{-1}$ 3164 m, 3102, 3040 w, 2953 m, 1671 s, 1596 m, 1484 m, 817 s; MS (ES): m/z=302.0 [M+H]$^+$; HRMS (ES) calcd. for C$_{11}$H$_{13}$NOI [M+H]$^+$: 302.0042, found: 302.0042. Found: C, 43.91; H, 4.02; N, 4.63. Calc. for C$_{11}$H$_{12}$NOI: C, 43.88; H, 4.02; N, 4.65%.

1.3 6-Iodo-4,4-dimethyl-1-(propan-2-yl)-1,2,3,4-tetrahydroquinolin-2-one (3)

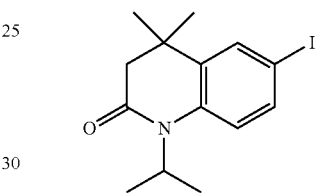

To a solution of compound 2 (25.9 g, 85.9 mmol) in anhydrous DMF (200 mL) was added crushed KOH (14.5 g, 257 mmol) and the resultant slurry stirred for 1 h at 50° C. under Ar. To this was added 2-iodopropane (25.6 mL, 257 mmol) and the solution stirred at 50° C. for 40 h under Ar. The reaction was quenched with H$_2$O, diluted with EtOAc, washed with sat. NH$_4$Cl, H$_2$O and brine, dried (MgSO$_4$) and evaporated to give a crude clear oil (29.0 g). This was purified by SiO$_2$ chromatography (hexane:EtOAc, 9:1, with 1% Et$_3$N, as eluent) to give compound 3 as a colourless oil (14.8 g, 50%): R$_f$ 0.51 (hexane:EtOAc, 8:2, with 1% Et$_3$N); $^1$H NMR (400 MHz, CDCl$_3$) δ 1.25 (s, 6H), 1.50 (d, J=7.0 Hz, 6H), 2.38 (s, 2H), 4.66 (sept, J=7.0 Hz, 1H), 6.87 (d, J=8.6 Hz, 1H), 7.50 (dd, J=8.6, 2.1 Hz, 1H), 7.52 (d, J=2.1 Hz, 1H); $^{13}$C NMR (101 MHz, CDCl$_3$) δ 20.3, 26.8, 33.1, 47.2, 48.8, 86.9, 119.0, 133.4, 135.9, 139.1, 139.3, 169.8; IR (neat) ν$_{max}$/cm$^{-1}$ 2961 m, 2934 w, 2870 w, 1667 s, 1582 m, 1482 m, 809 s; MS (ES): m/z=344.0 [M+H]$^+$; HRMS (ES) calcd. for C$_{14}$H$_{19}$NOI [M+H]$^+$: 344.0511, found: 344.0512. Found: C, 49.21; H, 5.29; N, 4.08. Calc. for C$_{14}$H$_{18}$NOI: C, 48.99; H, 5.29; N, 4.08%.

1.4 6-Iodo-4,4-dimethyl-1-(propan-2-yl)-1,2,3,4-tetrahydroquinoline (4)

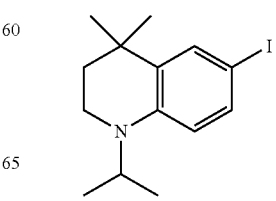

To a solution of compound 3 (1.25 g, 3.63 mmol) in anhydrous toluene (15 mL) was added borane dimethyl sulfide complex (2.0 M in THF, 1.91 mL, 3.81 mmol) dropwise and the resultant solution stirred at reflux for 16 h under Ar. The solution was cooled to RT, 10% aq. $Na_2CO_3$ (25 ml) added and then stirred for 0.5 h. The resultant solution was diluted with EtOAc, washed with $H_2O$ and brine, dried ($MgSO_4$) and evaporated to give a crude colourless oil (1.12 g). This was purified by $SiO_2$ chromatography (hexane:EtOAc, 9:1, with 1% $Et_3N$, as eluent) to give compound 4 as a colourless oil (1.08 g, 90%): $^1$H NMR (700 MHz, $CDCl_3$) δ 1.19 (d, J=6.6 Hz, 6H), 1.24 (s, 6H), 1.65-1.67 (m, 2H), 3.14-3.17 (m, 2H), 4.06 (sept, J=6.6 Hz, 1H), 6.46 (d, J=8.8 Hz, 1H), 7.28 (dd, J=8.9, 2.1 Hz, 1H), 7.39 (d, J=2.2 Hz, 1H); $^{13}$C NMR (176 MHz, $CDCl_3$) δ 18.9, 30.3, 32.4, 36.6, 36.8, 47.3, 76.1, 113.4, 134.5, 134.8, 135.6, 144.0; IR (neat) $v_{max}$/cm$^{-1}$ 2957 m, 2927 w, 2863 w, 1580 m, 1489 m, 792 s, 684 w; MS (ES): m/z=330.1 [M+H]$^+$; HRMS (ES) calcd. for $C_{14}H_{21}NI$ [M+H]$^+$: 330.0719, found: 330.0717.

1.5 4-Iodobenzenediazonium tetrafluoroborate (5)

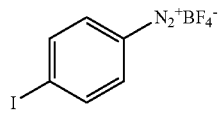

4-Iodoaniline (10.95 g, 50 mmol) was added to tetrafluoroboric acid solution (48% in $H_2O$, 25 mL), and the suspension was cooled to 0° C. before a solution of $NaNO_2$ (3.79 g, 55 mmol) in $H_2O$ (13.73 mL) was added dropwise with vigorous stirring so as to maintain the internal temperature below 5° C. After addition the suspension was further stirred for 1 h at 0° C., before the precipitated solid was isolated by filtration, washed with cold MeOH and dried to give a crude brown solid. This was dissolved in a minimal amount of acetone (around 55 mL), and to which $Et_2O$ was slowly added to precipitate a yellow solid. This was filtered, washed with cold $Et_2O$ and dried to give compound 5 as a pale yellow solid (13.13 g, 83%): $^1$H NMR (700 MHz, $(CD_3)_2SO$) δ 8.35 (d, J=9.0 Hz, 2H), 8.43 (d, J=9.0 Hz, 2H); $^{13}$C NMR (151 MHz, $(CD_3)_2SO$) δ 113.6, 115.1, 132.8, 140.2; IR (neat) $v_{max}$/cm$^{-1}$ 3090 w, 2282 s, 1548 m, 1461 w, 824 s, 523 m. Found: C, 22.83; H, 1.30; N, 8.83, Calc. for $C_6H_4BF_4IN_2$: C, 22.67; H, 1.27; N, 8.81%.

1.6 Methyl (2E)-3-(4-iodophenyl)prop-2-enoate (6)

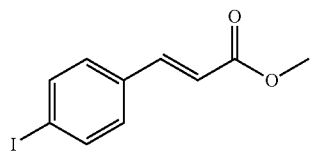

Pd(OAc)$_2$ (0.138 g, 0.61 mmol), $CaCO_3$ (2.40 g, 24.0 mmol) and compound 5 (5.54 g, 17.4 mmol) were suspended in MeOH (60 mL). Methyl acrylate (2.16 mL, 24.0 mmol) was added, and the suspension was stirred vigorously for 1.5 h. The solution was diluted with DCM, filtered through Celite and evaporated to give a crude light brown solid (6.3 g). This was purified by $SiO_2$ chromatography (hexane:DCM, 1:1, as eluent) to give compound 6 as a white solid (3.74 g, 75%): $^1$H NMR (600 MHz, $CDCl_3$) δ 3.81 (s, 3H), 6.44 (d, J=16.0 Hz, 1H), 7.24 (d, J=8.4 Hz, 2H), 7.60 (d, J=16.0 Hz, 1H), 7.73 (d, J=8.4 Hz, 2H); $^{13}$C NMR (151 MHz, $CDCl_3$) δ 52.0, 96.7, 118.8, 129.7, 134.1, 138.3, 143.8, 167.3; IR (neat) $v_{max}$/cm$^{-1}$ 3080 w, 3000 w, 2850 w, 1708 s, 1636 m, 1580 m, 1483 m, 815 s, 493 m; MS (ES): m/z=288.9 [M+H]$^+$; HRMS (ES) calcd. for $C_{10}H_{10}IO_2$ [M+H]$^+$: 288.9726, found: 288.9733. Found: C, 41.86; H, 3.14. Calc. for $C_{10}H_9IO_2$: C, 41.96; H, 3.15%.

1.7 Methyl (2E)-3-4-[2-(trimethylsilyl)ethynyl]phenylprop-2-enoate (7)

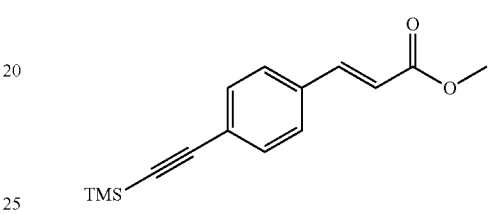

Triethylamine (80 mL) was added to an oven-dried Schlenk flask, and was then degassed via sonication under vacuum, followed by refilling with Ar (×5). Pd(PPh$_3$)$_2$Cl$_2$ (0.217 g, 0.31 mmol), CuI (0.06 g, 0.31 mmol) and compound 6 (3.57 g, 12.38 mmol) and trimethylsilylacetylene (1.76 mL, 12.44 mmol) were then added and the mixture was stirred at RT overnight. The solution was diluted with $Et_2O$, passed through Celite/$SiO_2$ under vacuum, and evaporated to give a light brown solid (4.5 g). This was purified by $SiO_2$ chromatography (hexane:EtOAc, 9:1, as eluent) to give compound 7 as a white solid (2.65 g, 83%): $^1$H NMR (400 MHz, $CDCl_3$) δ 0.25 (s, 9H) 3.80 (s, 3H), 6.42 (d, J=16.0 Hz, 1H), 7.40-7.50 (m, 4H), 7.64 (d, J=16.0 Hz, 1H).

1.8 Methyl (2E)-3-(4-ethynylphenyl)prop-2-enoate (8)

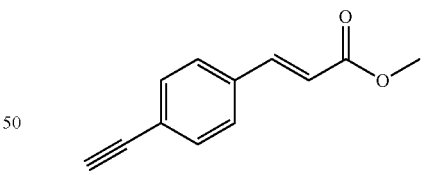

Compound 7 (2.21 g, 8.55 mmol) was dissolved in THF (25 mL), and cooled to −20° C. Tetrabutylammonium fluoride (1.0 M in THF, 8.98 mL, 8.98 mmol) was then added dropwise and the resultant solution stirred at −20° C. for 1 h, after which $H_2O$ was added, and the solution extracted with EtOAc (3×). The organics were washed with brine, dried ($MgSO_4$) and evaporated to give a crude brown solid. This was purified by $SiO_2$ chromatography (hexane:EtOAc, 9:1, as eluent) to give compound 8 as a white solid (1.52 g, 95%): m.p.=93-95° C.; $^1$H NMR (600 MHz; $CDCl_3$) δ 3.18 (s, 1H), 3.81 (s, 3H), 6.44 (d, J=16.0 Hz, 1H), 7.46-7.51 (m, 4H), 7.66 (d, J=16.0 Hz, 1H); $^{13}$C NMR (151 MHz; $CDCl_3$) δ 52.0, 79.4, 83.3, 119.1, 124.2, 128.1, 132.8, 134.9, 143.9, 167.4; IR (neat) $v_{max}$/cm$^{-1}$ 3260 m, 2996 w, 2946 w, 2108 w, 1700 s, 1634 m, 1554 m, 1431 m, 1206 s, 831 s; MS (EI): m/z=186.1 [M]$^+$. Found: C, 77.40; H, 5.37. Calc. for $C_{12}H_{10}O_2$: C, 77.40; H, 5.41%.

1.9 (2E)-3-(4-2-[4,4-Dimethyl-1-(propan-2-yl)-1,2,3,4-tetrahydroquinolin-6-yl]ethynylphenyl)prop-2-enoic Acid (9) (DC324)

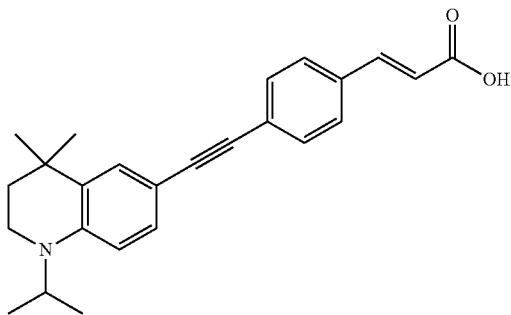 [SMILES: CC(C)N1CCC(C)(C)c2cc(C#Cc3ccc(/C=C/C(=O)O)cc3)ccc21]

Compound 4 (0.61 g, 1.85 mmol) was dissolved in triethylamine (12 mL), and the resultant solution was degassed by sonication under vacuum, before the atmosphere was replaced with Ar (5×). Pd(PPh$_3$)$_2$Cl$_2$ (0.13 g, 0.185 mmol), CuI (0.0352 g, 0.185 mmol) and compound 8 (0.362 g, 1.94 mmol) were then added under Ar. The resultant suspension was stirred at RT for 72 h. The suspension was diluted with hexane and passed through a thin Celite/SiO$_2$ plug (eluting with hexane, then hexane:EtOAc (8:2)). The extracts were washed with sat. NH$_4$Cl (3×), brine, dried (MgSO$_4$) and evaporated to give the coupling product as an orange solid (0.7 g). This was dissolved in THF (20 mL), 20% NaOH (2 mL) added, and the resultant solution was stirred under reflux for 40 h. The mixture was cooled, acidified to pH 1 with 5% HCl, diluted with EtOAc, washed with sat. NaHCO$_3$, H$_2$O and brine, dried (MgSO$_4$) and evaporated to give a crude yellow solid which was recrystallised from MeOH to give compound 9 as an orange crystalline solid (0.46 g, 67% over two steps): $^1$H NMR (700 MHz; (CD$_3$)$_2$SO) δ 1.16 (d, J=6.6 Hz, 6H)), 1.22 (s, 6H), 1.60-1.65 (m, 2H), 3.16-3.21 (m, 2H), 4.14 (hept, J=6.6 Hz, 1H), 6.54 (d, J=16.0 Hz, 1H), 6.69 (d, J=9.4 Hz, 1H), 7.17 (dd, J=8.6, 2.1 Hz, 1H), 7.29 (d, J=2.2 Hz, 1H), 7.46-7.51 (m, 2H), 7.58 (d, J=16.0 Hz, 1H), 7.66-7.72 (m, 2H), 12.41 (s, 1H); $^{13}$C NMR (176 MHz; (CD$_3$)$_2$SO) δ 18.6, 29.7, 31.6, 35.9, 36.1, 46.6, 86.9, 94.0, 106.8, 110.5, 119.5, 125.2, 128.4, 128.8, 130.6, 131.1, 131.2, 133.3, 143.0, 144.5, 167.5; MS(ES): m/z=374.2 [M+H]$^+$; HRMS (ES) calcd. for $C_{25}H_{28}NO_2$ [M+H]$^+$: 374.2120, found 374.2118.

Example 2

(2E)-3-(4-{2-[4,4-Dimethyl-1-(prop-2-yn-1-yl)-1,2,3,4-tetrahydroquinolin-6-yl]ethynyl}phenyl)prop-2-enoic Acid (15) (DC474)

2.1 (3-Bromoprop-1-yn-1-yl)trimethylsilane (10)

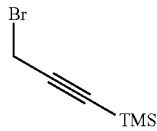

A solution of propargyl bromide (80% in toluene, 6.69 mL, 60.0 mmol) in THF (75 mL) was cooled to −78° C. under Ar. Lithium bis(trimethylsilyl)amide (10.37 g, 62.0 mmol) was added under Ar, and the solution then stirred for 0.5 h. Chlorotrimethylsilane (10.15 mL, 80.0 mmol) was then added dropwise, and the solution stirred for 0.5 h, whereupon sat. NH$_4$Cl (30 mL) was added, and the solution then warmed to RT. The solution was diluted with EtOAc, washed with brine, dried (MgSO$_4$) and evaporated to give a crude oil. This was purified by SiO$_2$ chromatography (hexane as eluent), and then further purified by Kugelrohr distillation (70-90° C., ambient pressure) to give compound 10 as a clear oil (8.09 g, 70%): $^1$H NMR (400 MHz; CDCl$_3$) δ 0.18 (s, 9H), 3.91 (s, 2H); $^{13}$C NMR (101 MHz; CDCl$_3$) δ −0.1, 14.9, 92.5, 100.2; IR (neat) $v_{max}$/cm$^{-1}$ 2960 w, 2906 w, 2180 w, 1251 m, 1204 m, 1038 m, 837 s; MS(EI): m/z=174.9 [M-CH$_3$]$^+$.

2.2 6-Iodo-4,4-dimethyl-1,2,3,4-tetrahydroquinoline (11)

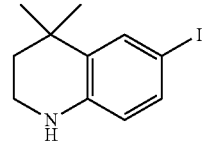

To a solution of compound 2 (4.00 g, 13.28 mmol) in anhydrous toluene (30 mL) was added borane dimethyl sulfide complex (2.0 M in THF, 8.30 mL, 16.6 mmol) dropwise and the resultant solution stirred under reflux for 16 h. The solution was cooled to RT, 10% aq. Na$_2$CO$_3$ (25 ml) added and the solution stirred for 0.5 h. The solution was then diluted with EtOAc, washed with brine, dried (MgSO$_4$) and evaporated to give a crude red oil. This was purified by SiO$_2$ chromatography (hexane:EtOAc, 9:1, with 1% Et$_3$N, as eluent) to give compound 11 as a colourless oil (3.36 g, 88%): $^1$H NMR (700 MHz; CDCl$_3$) δ 1.27 (s, 6H), 1.68-1.71 (m, 2H), 3.28-3.32 (m, 2H), 3.93 (br, 1H), 6.24 (d, J=8.4 Hz, 1H), 7.19 (dd, J=8.4, 2.0 Hz, 1H), 7.41 (d, J=2.1 Hz, 1H); $^{13}$C NMR (176 MHz; CDCl$_3$) δ 30.9, 32.0, 36.8, 38.4, 77.7, 116.5, 133.1, 135.1, 135.3, 143.4; IR (neat) $v_{max}$/cm$^{-1}$ 3400 br, 2956 w, 2927 w, 2862 w, 1589 m, 1524 m, 1492 s, 1352 m, 1282 s, 804 s; MS(ES): m/z=288.0 [M+H]$^+$; HRMS (ES) calcd. for $C_{11}H_{15}NI$ [M+H]$^+$: 288.0246, found 288.0242.

2.3 6-Iodo-4,4-dimethyl-1-[3-(trimethylsilyl)prop-2-yn-1-yl]-1,2,3,4-tetrahydroquinoline (12)

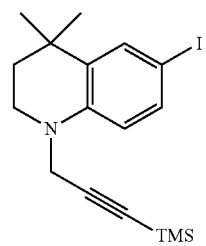 [SMILES: CC1(C)CCN(CC#C[Si](C)(C)C)c2ccc(I)cc21]

K$_2$CO$_3$ (1.39 g, 10.08 mmol) was added to a solution of compound 11 (2.07 g, 7.20 mmol) in anhydrous DMF (25 mL) under Ar and the resultant slurry was stirred for 1 h.

Compound 10 (1.65 mL, 10.08 mmol) was added, and the solution was stirred at RT for 72 h. The solution was diluted with H$_2$O, and extracted with EtOAc (3×). The organics were washed with sat. NH$_4$Cl, H$_2$O and brine, dried (MgSO$_4$) and evaporated to give a crude yellow oil. This was purified by SiO$_2$ chromatography (hexane:EtOAc, 96:4, with 1% Et$_3$N as eluent) to give compound 12 as a light yellow oil (2.71 g, 95%): $^1$H NMR (700 MHz; CDCl$_3$) δ 0.13 (s, 9H), 1.26 (s, 6H), 1.74-1.78 (m, 2H), 3.27-3.31 (m, 2H), 3.99 (s, 2H), 6.49 (d, J=8.7 Hz, 1H), 7.33 (dd, J=8.7, 2.2 Hz, 1H), 7.42 (d, J=2.2 Hz, 1H); $^{13}$C NMR (176 MHz, CDCl$_3$) δ 0.2, 30.7, 32.4, 36.9, 42.0, 45.6, 78.8, 89.0, 101.4, 114.7, 134.6, 135.5, 135.5, 143.3; IR (neat) $v_{max}$/cm$^{-1}$ 2958 w, 2925 w, 2856 w, 2169 w, 1584 m, 1491 m, 1332 m, 1248 m, 838 s; MS(ES): m/z=288.0 [M+H]$^+$; HRMS (ES) calcd. for C$_{17}$H$_{25}$SiNI [M+H]$^+$: 398.0801, found 398.0797.

2.4 Methyl (2E)-3-[4-(2-{4,4-dimethyl-1-[3-(trimethylsilyl)prop-2-yn-1-yl]-1,2,3,4-tetrahydroquinolin-6-yl})ethynyl)phenyl]prop-2-enoate (13)

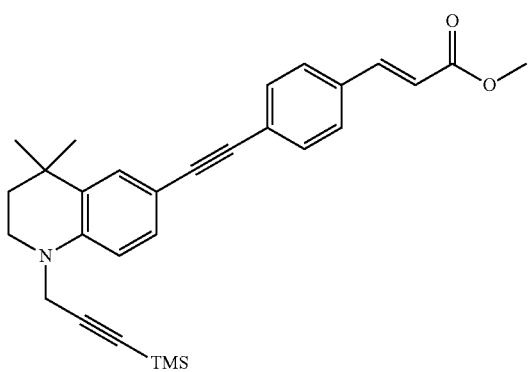 [SMILES: COC(=O)/C=C/c1ccc(C#Cc2ccc3c(c2)C(C)(C)CCN3CC#C[Si](C)(C)C)cc1]

Compound 12 (1.61 g, 4.05 mmol) was dissolved in triethylamine (35 mL), and the resultant solution was degassed by sonication under vacuum, before the atmosphere was replaced with Ar (5×). Pd(PPh$_3$)$_2$Cl$_2$ (0.28 g, 0.405 mmol), CuI (0.077 g, 0.405 mmol) and compound 8 (0.79 g, 4.25 mmol) were then added under Ar. The resultant suspension was stirred at RT for 72 h. The suspension was diluted with hexane and passed through a thin Celite/SiO$_2$ plug (eluting with hexane, then Et$_2$O). The extracts were washed with sat. NH$_4$Cl (3×), brine, dried (MgSO$_4$) and evaporated to give the coupling a crude yellow oil. This was purified by SiO$_2$ chromatography (hexane:EtOAc, 9:1, with 1% Et$_3$N as eluent) to give compound 13 as a thick yellow oil (1.25 g, 68%): $^1$H NMR (700 MHz, CDCl$_3$) δ 0.12 (s, 9H), 1.30 (s, 6H), 1.77-1.80 (m, 2H), 3.34-3.37 (m, 2H), 3.81 (s, 3H), 4.05 (s, 2H), 6.43 (d, J=16.0 Hz, 1H), 6.68 (d, J=8.6 Hz, 1H), 7.27 (dd, J=8.5, 2.0 Hz, 1H), 7.38 (d, J=2.0 Hz, 1H), 7.45-7.52 (m, 4H), 7.67 (d, J=16.0 Hz, 1H); $^{13}$C NMR (176 MHz, CDCl$_3$) δ 0.2, 30.5, 32.3, 36.9, 42.0, 45.7, 51.9, 87.3, 89.0, 93.8, 101.3, 110.5, 112.2, 118.0, 126.5, 128.2, 129.6, 130.8, 131.8, 132.5, 133.4, 144.1, 144.4, 167.6; IR (neat) $v_{max}$/cm$^{-1}$ 3042 w, 2957 w, 2927 w, 2858 w, 2195 w, 1718 s, 1634 m, 1595 s, 1515 s, 1324 s, 1170 s, 842 s; MS(ES): m/z=456.2 [M+H]$^+$; HRMS (ES) calcd. for C$_{26}$H$_{26}$NO$_2$ [M+H]$^+$: 456.2359, found 456.2345.

2.5 Methyl (2E)-3-(4-2-[4,4-dimethyl-1-(prop-2-yn-1-yl)-1,2,3,4-tetrahydroquinolin-6-yl]ethynyl)phenyl)prop-2-enoate (14) (DC473)

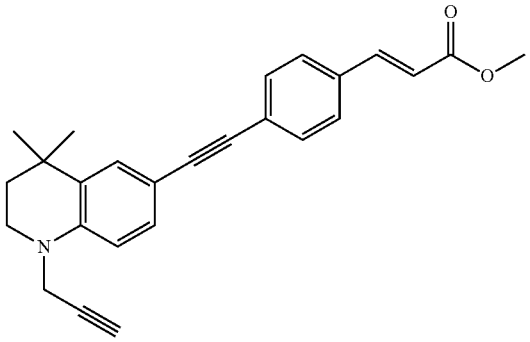 [SMILES: C#CCN1CCC(C)(C)c2cc(C#Cc3ccc(/C=C/C(=O)OC)cc3)ccc21]

Compound 13 (1.20 g, 2.64 mmol) was dissolved in THF (30 mL), and cooled to −20° C. Tetrabutylammonium fluoride (1.0 M in THF, 2.90 mL, 2.90 mmol) was then added dropwise and the resultant solution stirred at −20° C. for 1 h, after which H$_2$O was added, and the solution extracted with EtOAc (3×). The organics were washed with brine, dried (MgSO$_4$) and evaporated to give a crude solid. This was purified by SiO$_2$ chromatography (hexane:EtOAc, 8:2, with 1% Et$_3$N as eluent) to give compound 14 as a yellow oil that slowly crystallises to give an orange solid (0.83 g, 82%): m.p.=101-102° C.; $^1$H NMR (400 MHz, CDCl$_3$) δ 1.30 (s, 6H), 1.76-1.83 (m, 2H), 2.16-2.20 (m, 1H), 3.33-3.39 (m, 2H), 3.81 (s, 3H), 4.05 (d, J=2.4 Hz, 2H), 6.43 (d, J=16.0 Hz, 1H), 6.68 (d, J=8.6 Hz, 1H), 7.28 (dd, J=8.5, 1.9 Hz, 1H), 7.39 (d, J=1.9 Hz, 1H), 7.43-7.54 (m, 4H), 7.67 (d, J=16.0 Hz, 1H); $^{13}$C NMR (101 MHz, CDCl$_3$) δ 30.7, 32.3, 36.9, 41.0, 45.9, 51.9, 72.0, 79.3, 87.3, 93.7, 110.9, 111.9, 118.0, 126.5, 128.2, 129.8, 130.8, 131.9, 132.6, 133.5, 143.9, 144.4, 167.6; IR (neat) $v_{max}$/cm$^{-1}$ 3288 w, 2954 w, 2927 w, 2861 w, 2194 m, 1716 s, 1633 m, 1595 s, 1515 s, 1496 m, 1324 s, 1170 s, 830 s; MS(ES): m/z=384.4 [M+H]$^+$; HRMS (ES) calcd. for C$_{26}$H$_{26}$NO$_2$ [M+H]$^+$: 384.1964, found 384.1963.

2.6 (2E)-3-(4-{2-[4,4-Dimethyl-1-(prop-2-yn-1-yl)-1,2,3,4-tetrahydroquinolin-6-yl]ethynyl}phenyl)prop-2-enoic Acid (15) (DC474)

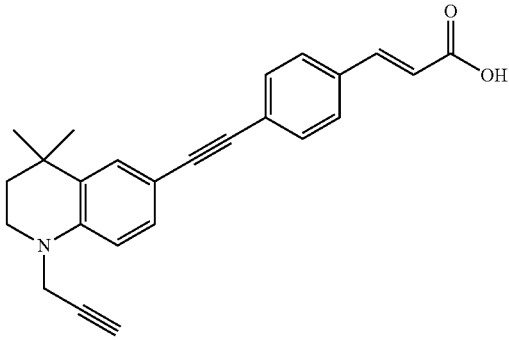 [SMILES: C#CCN1CCC(C)(C)c2cc(C#Cc3ccc(/C=C/C(=O)O)cc3)ccc21]

Compound 14 (0.824 g, 2.15 mmol) was dissolved in THF (25 mL), 20% NaOH (2.5 mL) added, and the resultant solution was stirred under reflux for 40 h. The mixture was cooled, acidified to pH 1 with 5% HCl, diluted with EtOAc, washed with sat. NH$_4$Cl, H$_2$O and brine, dried (MgSO$_4$) and evaporated to give a crude yellow solid which was recrystallised from MeCN to give compound 15 as an orange crystalline solid (0.50 g, 63%): m.p.=193-195 OC (decomposition); $^1$H NMR (400 MHz, (CD$_3$)$_2$SO) δ 1.24 (s, 6H), 1.69-1.75 (m, 2H), 3.12 (t, J=2.3 Hz, 1H), 3.27-3.32 (m, 2H), 4.14 (d, J=2.3 Hz, 2H), 6.55 (d, J=16.0 Hz, 1H), 6.74 (d, J=8.7 Hz, 1H), 7.23 (dd, J=8.5, 2.0 Hz, 1H), 7.35 (d, J=2.1 Hz, 1H), 7.49-7.53 (m, 2H), 7.59 (d, J=16.0 Hz, 1H), 7.68-7.72 (m, 2H), 12.44 (s, 1H); $^{13}$C NMR (101 MHz, (CD$_3$)$_2$SO) δ 30.3, 31.6, 36.0, 44.8, 74.3, 79.8, 87.1, 93.4, 109.2, 112.2, 119.7, 124.9, 128.4, 129.1, 130.2, 131.2, 132.1, 133.5, 143.0, 143.9, 167.5; IR (neat) $\nu_{max}$/cm$^{-1}$ 3278 w, 2962 w, 2920 w, 2847 w, 2196 w, 1684.9, 1623n, 1515n, 1217 s, 836 w; MS(ES): m/z=370.8 [M+H]$^+$; HRMS (ES) calcd. for C$_{25}$H$_{24}$NO$_2$ [M+H]$^+$: 370.1807, found 370.1804.

Example 3

3.1 Example Click Conjugation of Compound 15 (DC474) with Benzyl Azide to Give Methyl (2E)-3-[4-(2-{1-[(1-benzyl-1H-1,2,3-triazol-4-yl)methyl]-4,4-dimethyl-1,2,3,4-tetrahydroquinolin-6-yl}ethynyl)phenyl]prop-2-enoate (16)

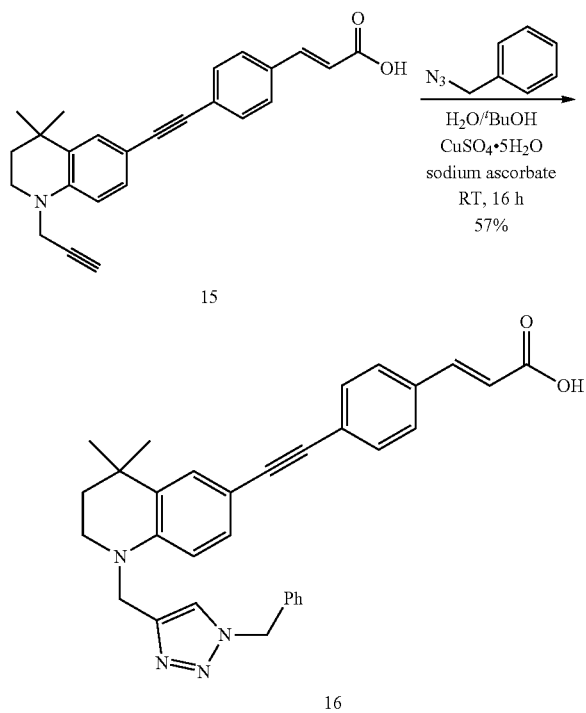

Compound 15 (75 mg, 0.203 mmol) and benzyl azide (0.028 mL, 0.223 mmol) were suspended in H$_2$O/BuOH (1:1, 1 mL), before sodium ascorbate (1M in H$_2$O, 0.020 mL, 0.02 mmol) and CuSO$_4$.5H$_2$O (5 mg, 0.02 mmol) were added. The suspension was stirred vigorously for 16 h, before being diluted with cold H$_2$O, and the precipitated solid was filtered and dried to give compound 16 as a yellow solid (59 mg, 57%). $^1$H NMR indicated 87% conversion to compound 16.

Example 4

4.1 Cell Culture and Media

Immortalised HaCaT cell lines were maintained in Dulbecco's Modified Eagle's Medium (5 mL) containing 10% Foetal Bovine Serum and 1% Penicillin Streptomycin antibiotic.

4.2 Fixed Cell Imaging

HaCaT human keratinocyte cells were seeded onto acid washed glass coverslips and treated, with a single dose, of either a 1 μM or a 10 μM solution of the compound. They were left in this compound containing media for 2 to 72 h before live-staining with Mitotracker red or BODIPY® TR Ceramide complexed to BSA. The cells were then fixed with 4% PFA, and mounted onto glass slides with Mowiol®. Images were taken on a Zeiss LSM 880 microscope. Note: these experiments were also carried out using a mouse embryonic fibroblast cell line, J2. However, some background fluorescence was present in J2 s at the same wavelengths as the compound. Therefore, HaCaTs were favoured for imaging.

Treatment with Compounds

An acid washed glass coverslip was placed in the bottom of each well of a 24 well plate. In each well, HaCaT cells (12,000 approx.) were seeded in serum containing media (1 mL) and allowed 24 h to settle before being treated. The media was replaced with media containing the compound/DMSO control (1 mL). For the 10 μM wells, compound (10 μL, 1 mM) was added to serum containing media (9990 μL). For the 1 μM wells, compound (1 μL, 1 mM) was added to serum containing media (9999 μL). The cells were stained and fixed 72 h or 48 h after being treated with the compound. The appropriate vehicle only experimental controls were included.

MitoTracker® red staining: The cells were incubated for 30 min with MitoTracker® Red diluted in serum containing media (1 mL, 0.1 μM). They were then rinsed twice with PBS before incubation with PFA (0.5 mL, 4%), for 5 min. Cells were rinsed in PBS before mounting onto glass slides with Mowiol®.

BODIPY® TR Ceramide complexed to BSA staining: The cells were incubated for 30 min at 4° C. with BODIPY® TR Ceramide complexed to BSA diluted in PBS (1 mL, 5 μM). They were then rinsed twice with cold PBS before incubation in fresh PBS at 37° C. for a further 30 min. The cells were fixed by incubation with PFA (0.5 mL, 4%), for 5 min. Cells were rinsed in PBS before mounting onto glass slides with Mowiol®.

Imaging: Images taken using the Zeiss LSM 880 AxioObserver confocal microscope, with the Plan-Apochromat 63x/1.4 Oil DIC M27 objective lens. Acquisition settings can be found in table 1.

TABLE 1

| Acquisition Settings | | |
|---|---|---|
| | Green Channel (Compound) | Red Channel (Stain) |
| Detection wavelength/nm | 431-560 | 600-735 |
| Excitation wavelength/nm | 405 | 594 |
| Emission wavelength/nm | 460 | 668 |

TABLE 1

Absorption and fluorescence emission maxima of dyes, in nm, determined in methanol

|  | BODIPY® TR Ceramide complexed to BSA | MitoTracker® Red |
|---|---|---|
| Absorbance wavelength/nm | 589 max<br>300-640 range | 579 max<br>300-630 range |
| Emission wavelength/nm | 617 max<br>575-724 range | 599 max<br>560-700 range |

TABLE 3

Absorbance and emission spectra data

|  | DC324<br>(In chloroform, excitation at 400 nm) | DC473<br>(In chloroform, excitation at 380 nm) | DC474<br>(In chloroform, excitation at 300 nm) |
|---|---|---|---|
| Absorbance wavelength/nm | 400 max<br>275-475 range | 380 max<br>275-450 range | 380 max<br>275-450 range |
| Emission wavelength/nm | 560 max<br>450-700 range | 520 max<br>440-680 range | 540 max<br>450-700 range |

Example 5

Living Cell Imaging

5.1 Cell Death on Zeiss Live Cell Observer

One day prior to imaging, HaCaT or J2 cells (20,000 approx.) were seeded into each well of a 6 well or 24 well plastic plate. Cells were allowed to incubate overnight in serum containing media. One to four hours before imaging the normal media was replaced with compound containing media, 1 mL per well. The cells were imaged in a 37° C. heated chamber and supplied with 5% $CO_2$. Zeiss Live Cell Observer microscope: OSRAM 1×HBO 103 W/2 100 Watt Mercury Bulb, DAPI Excitation filter=335-385 nm, DAPI Emission filter=420-470 nm. Note: Cells were imaged in DMEM media which contains phenol red.

5.2 Cell Death on Zeiss 880 Confocal

One day prior to imaging, HaCaT cells (4000 approx.) were seeded into each well of an 8 well glass slide. Cells were allowed to incubate overnight in serum containing media. One hour before imaging the normal media was replaced with compound containing media, 1 mL per well. The cells were imaged in a 37° C. heated chamber using the Zeiss LSM 880 with Airyscan confocal laser scanning microscope. Note: Cells were imaged in DMEM media which contains phenol red.

5.3 ROS Staining

One day prior to imaging, HaCaT cells (20,000 approx) were seeded into each well of a 24 well plastic plate. Cells were allowed to incubate overnight in serum containing media. Three hours prior to imaging, the media in each well was replaced with fresh serum containing media which included a 1:500 dilution of Superoxide Detection Reagent, CellRox. Note: A 1:2500 dilution was originally tried and was less effective. The cells were incubated with the ROS stain at 37° C. for one hour. An hour and a half before imaging, the media in the negative control well was replaced with N-acetyl-L-cysteine diluted in serum containing media (1 mL, 10 mM). One hour before imaging the media in all but one of the other wells was replaced with compound containing media, 1 mL per well. Thirty minutes prior to imaging, the media in the positive control well was replaced with pyocyanine diluted in serum containing media (1 mL, 500 µM). Pyocyanine induces ROS within 20-30 minutes. The cells were imaged in a heated chamber and supplied with 5% $CO_2$. The cells were imaged in a 37° C. heated chamber using the Zeiss LSM 880 with Airyscan confocal laser scanning microscope. Cells were irradiated with 405 nm laser to activate compounds and ROS dye was excited with 633 nm laser Note: Cells were imaged in DMEM media which contains phenol red.

6. Results

6.1 Initial Screening of Compounds

Following exposure to UV light, no membrane blebbing was observed in ATRA, EC23 and DMSO treated cells. DC324 and DC473 induced membrane blebbing and cell death following exposure to UV light.

6.2 DC324

DC324 was not observed filling the nucleus.

Referring to FIG. 3: DC324 localised to one side of the nucleus in large patches of cells. DC324 emits above zero fluorescence in the 405-640 range. The red channel was recorded 600-735 nm. This image shows signs of DC324 emission in the red channel.

Referring to FIG. 4: DC324 co-imaged with BODIPY® Golgi stain. Some regions show overlap between the Golgi and DC324. DC324 appears to be entering the nucleus in one of these cells. Cells fixed after 72 hours in 1 µM DC324.

6.3 Cell Death

6.3.1 UV Light

Referring to FIG. 5: DC324 was the most rapid inducer of cell death. A single 10 s treatment with UV light was sufficient to induce necrosis in 10 µM DC324 treated cells, within two hours using a 10× objective lens and at Phase 0. Part C shows healthy cells from the same well, in an area away from the site of UV exposure. The localised effect of the UV light indicates that the cell death is not due to heat transfer.

Referring to FIG. 6: Cell death observations were consistent across different cell lines. DC324 treated J2 cells, a mouse fibroblast cell line, displayed membrane blebbing within two hours following a single UV treatment. UV untreated cells appear healthy after 26 hours in the compound in the same well as the treated area. This suggests that the cause of death is localised, not due to heat transfer, and due to the combined effect of the UV light and the DC324. A 10× objective lens at Phase 0 was used.

6.3.2 405 nm Light

Images of 10 µM compound treated cells were taken every twenty minutes and at each time point a treatment of 405 nm light at 50% laser strength was applied. Cell death was not as rapid under the 405 nm laser light as under the UV light, only DC324 was significantly different to the DMSO control.

Referring to FIG. 7: The majority of DMSO treated cells appeared healthy after 47 exposures to 405 nm laser, at 50% strength. No membrane blebbing was observed.

Referring to FIG. 8: The majority of ATRA treated cells appeared healthy after 47 exposures to 405 nm laser, at 50% strength. No membrane blebbing was observed.

Referring to FIG. 9: Membrane blebbing was induced in DC324 treated cells by 405 nm laser, at 50% strength. The first bleb appeared after 21 exposures, however, the majority of cells presented membrane blebbing between 30 and 40 exposures. The cell death induced by 405 nm light appeared more characteristic of apoptosis than the cell death caused by UV light. Cells appeared to shrink rather than expand, and apoptotic bodies are visible.

Referring to FIG. 10: DC324 treated cells putatively producing apoptotic bodies. This is an image from the same experiment discussed previously. It was taken at the 37$^{th}$ exposure to 405 nm light, 740 minutes from the first exposure, and 770 minutes after the addition of DC324. A number of the cells appear to be releasing small spheres from all edges.

Referring to FIG. 11: DC324 fluorescence from treated HaCaT cells, imaged with 405 nm laser light, at 50% strength. Initially, DC324 is brightest around the edges of the cells. DC324 is then concentrated to the centre of the cells and is also visible in the membrane blebs.

6.4 Dose Response

The speed of death was tested at a number of concentrations in order to determine an estimate for the $EC_{50}$ (half maximal effective concentration) value. Morphological changes were recorded using time lapse imaging at 5 minute intervals. The time taken between 10 s of UV light treatment and the first sign of damage to the cell membranes was recorded. Each cell in the field of view was treated as an individual data point, before taking an average of the time for each concentration.

Referring to FIG. 12: The dose-dependent response of HaCaT cells treated with DC324 and DC473 and 10 seconds of UV. UV exposure was administered through the DAPI filter and a 20× objective lens, phase 0. $EC_{50}$ values for both compounds were determined based on the average viable fraction of the cellular population 24 hours after the initial irradiation event of 0.20 (±0.007) μM and 0.18 (±0.006) μM for DC324 and DC473, respectively.

6.5 ROS Staining

Referring to FIG. 13: Control treatments stained for superoxide after exposure to UV. Staining for superoxide production under the rhodamine filter. Fluorescence in the negative control indicates possible background fluorescence from HaCaT cells. One cell in the negative control is induced to produce increased fluorescence post-UV imaging. This could be due to an increase in superoxide production in an apoptotic cell, or merely due to the change in shape of the cell as it dies. The positive control treated cells were visibly rounded and dying when imaged under phase. Therefore, the reactive oxygen species had already been produced before the imaging began. However, the superoxide stain was brighter for the positive control, indicating that superoxide was still present. Several smaller patches of the DMSO treated cells showed superoxide production prior to exposure to UV, these cells were most affected by the DAPI treatment. Compared with the initial picture taken 60 seconds after UV treatment, the image taken 260 seconds after UV treatment shows that there is an increase in fluorescence in a defined circle in the centre of these cells.

Referring to FIG. 14: Active compounds stained for superoxide after exposure to DAPI. As seen with the DMSO control, the ATRA treated cells which already had some evidence of superoxide production before UV treatment produced an increased level of fluorescence post exposure to UV. As with the DMSO control, this fluorescence formed a defined circle in the centre of the cell, 260 seconds after exposure to UV. For all treatments, healthy normal cells produced a brighter fluorescence in small circles in the cell.

Referring to FIG. 15: DC324 compound treated cells stained for superoxide after UV exposure. The intensity of the small bright circles in the centre of the cells increased 60 seconds after UV treatment, compared with before exposure. This indicates superoxide production. This initial increase in brightness faded as the ROS dye photo-bleaches. Imaging the ROS dye under the rhodamine filter induced photo-bleaching much more rapidly with the DC324 treated cells than with the other compounds.

In order to gain more insight into the mode of action leading to cell death, we examined the photo-initiated ROS production using the redox reactive dye, CellRox, which fluoresces in response to oxidation by reactive oxygen species. DC324-treated cells stimulated with 405 nm light exhibited a strong CellRox fluorescence signal after irradiation, particularly in intracellular organelles. CellRox fluorescence was quantified in the cell before and after irradiation; a steady increase in the production of ROS-stimulated relative fluorescence was observed immediately following irradiation in DC324-treated cells, but not cells treated with EC23, a synthetic retinoid analogue of DC324 with ATRA-like biochemical properties, which acted as a negative control, to demonstrate that co-treatment with any retinoid or near ATRA-like analogue and light does not kill cells.

Referring to FIG. 16 DC473 compound treated cells after 2 hours and 24 hours UV exposure.

Referring to FIG. 17 a comparison is made of DC324 and DC473 compound treated cells.

Referring to FIG. 18 a comparison is made between the absorption spectra of DC324, DC473 and DC474 in $CHCl_3$.

Referring to FIG. 19 a comparison is made between the emission spectra of DC324, DC473 and DC474 in $CHCl_3$.

Referring to FIG. 20 a comparison is made between the absorption spectra of DC473, DC474 and click-conjugate compound 16 in $CHCl_3$.

Referring to FIG. 21 a comparison is made between the emission spectra of DC473, DC474 and click-conjugate compound 16 in $CHCl_3$.

REFERENCES

1 R. Comitato, T. Esposito, G. Cerbo, F. Angelini, B. Varriale and A. Cardone, *J. Exp. Zool. A. Comp. Exp. Biol.*, 2006, 305, 288-98.

2 D.-D. Lee, O. Stojadinovic, A. Krzyzanowska, C. Vouthounis, M. Blumenberg and M. Tomic-Canic, *J. Cell. Physiol.*, 2009, 220, 427-39.

3 M. Ethirajan, Y. Chen, P. Joshi and R. K. Pandey, *Chem. Soc. Rev.*, 2011, 40, 340-62.

4 S. Grether-Beck, S. Olaizola-Horn, H. Schmitt, M. Grewe, A. Jahnke, J. P. Johnson, K. Briviba, H. Sies and J. Krutmann, *Proc. Natl. Acad. Sci.*, 1996, 93, 14586-14591.

5 I. Mfouo-Tynga and H. Abrahamse, *Int. J. Mol. Sci.*, 2015, 16, 10228-41.

6 Z. Wang, M. Boudjelal, S. Kang, J. J. Voorhees and G. J. Fisher, *Nat. Med.*, 1999, 5, 418-22.

7 H.-U. Simon, A. Haj-Yehia and F. Levi-Schaffer, *Apoptosis*, 5, 415-418.

8 Ryan F. Donnelly, Paul A. McCarron, and A. David Woolfson, Perspect Medicin Chem. 2007; 1: 49-63. Published online 2007 Dec. 11; PMCID: PMC2754918 "Derivatives of 5-Aminolevulinic Acid for Photodynamic Therapy".

9 Leanne B. Josefsen and Ross W. Boyle, Met Based Drugs. 2008; 2008: 276109; Published online 2008 Sep. 11; doi:10.1155/2008/276109; PMCID: PMC2535827 "Photodynamic Therapy and the Development of Metal-Based Photosensitisers".

The invention claimed is:

1. A compound of formula I:

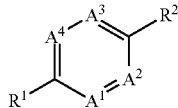

I in which
A$^1$ is N or CR$^3$;
A$^2$ is N or CR$^4$;
A$^3$ is N or CR$^5$;
R$^3$, R$^4$ and R$^5$, which may be the same or different, are each hydrogen, alkyl$_{C1-10}$, alkene$_{C2-12}$, aryl, aralkyl, halogen, trifluoroalkyl, cyano, nitro, —NR$^a$R$^b$, —OR$^a$, glycol, —C(O)R$^a$, —C(O)OR$^a$, —OC(O)R$^a$, —S(O)R$^a$R$^b$, —C(O)NR$^a$R$^b$ or a solubilising group;
R$^7$ is hydrogen, propynyl, —(CH$_2$)$_n$C≡CH, —(CH$_2$)$_n$SH, —(CH$_2$)$_n$SO$_2$F or —(CH$_2$)$_n$C=CH$_2$, alkyl$_{C1-10}$, said alkyl being optionally substituted by aryl or heteroaryl;
R$^8$, R$^9$, R$^{10}$ and R$^{11}$, which may be the same or different, are each hydrogen or alkyl$_{C1-4}$, aryl, halogen, trifluoroalkyl, —OR$^c$ or glycol, or together one pair of R$^8$ and R$^{10}$ or R$^9$ and R$^{11}$ represent a bond;
R$^{12}$ and R$^{13}$, which may be the same or different, are each hydrogen, alkyl$_{C1-4}$ or together one pair of R$^{10}$ and R$^{12}$ or R$^{11}$ and R$^{13}$ represent a bond, or R$^{12}$ and R$^{13}$ together form a group:

provided that the pair of R$^{10}$ and R$^{12}$ or R$^{11}$ and R$^{13}$ does not represent a bond if a pair from R$^8$, R$^9$, R$^{10}$ and R$^{11}$ represents a bond;
R$^{14}$ and R$^{15}$, which may be the same or different, are each hydrogen or alkyl$_{C1-10}$; and
R$^a$, R$^b$ and R$^c$, which may be the same or different, are each hydrogen or alkyl$_{C1-10}$;
n is an integer from 1 to 6;
R$^2$ is a group III:

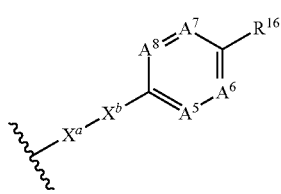

III in which
X$^a$ is —C≡C—, —CH=CH— or —N=CH—;
X$^b$ is —C≡C— or is absent;
A$^5$ is N or CR$^{17}$;
A$^6$ is N or CR$^{18}$;
A$^7$ is N or CR$^{19}$;
A$^8$ is N or CR$^{20}$;
R$^{17}$, R$^{18}$, R$^{19}$ and R$^{20}$, which may be the same or different, are each hydrogen, alkyl$_{C1-10}$, alkene$_{C2-12}$, aryl, aralkyl, halogen, trifluoroalkyl, cyano, nitro, —NR$^d$R$^e$, —OR$^d$, glycol, —C(O)R$^d$, —C(O)OR$^d$, —OC(O)R$^d$, —S(O)R$^d$R$^e$, —C(O)NR$^d$R$^e$ or a solubilising group;
R$^{16}$ is —CR$^{21}$=CR$^{22}$Y, —C≡C—R$^{23}$ or together with R$^{18}$ forms a ring IV:

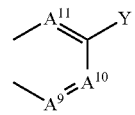

IV

A$^9$ is N or CR$^{24}$;
A$^{10}$ is N or CR$^{25}$;
A$^{11}$ is N or CR$^{26}$;
R$^{23}$ is a group V:

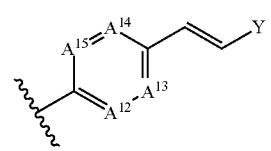

V in which
A$^{12}$ is N or CR$^{27}$;
A$^{13}$ is N or CR$^{28}$;
A$^{14}$ is N or CR$^{29}$;
A$^{15}$ is N or CR$^{30}$;
R$^{21}$ and R$^{22}$, which may be the same or different, are each hydrogen, alkyl$_{C1-10}$, alkene$_{C2-12}$, aryl, halogen or trifluoroalkyl;
R$^{24}$, R$^{25}$, R$^{26}$, R$^{27}$, R$^{28}$, R$^{29}$ and R$^{30}$, which may be the same or different, are each hydrogen, alkyl$_{C1-10}$, alkene$_{C2-12}$, aryl, halogen, trifluoroalkyl, —OR$^f$, glycol or a solubilising group;
R$^d$, R$^e$ and R$^f$, which may be the same or different, are each hydrogen or alkyl$_{C1-10}$;
Y is —CO$_2$R$^{31}$, —COH, —CO$_2$CH$_2$C≡CH, —CN, —SF$_5$, —SO$_3$H, —SO$_2$NH$_2$, —SO$_2$CF$_3$, —CF$_3$, —CO$_2$(CH$_2$)$_m$SH, —CO$_2$(CH$_2$)$_m$SO$_2$F, —CO$_2$(CH$_2$)$_m$CH=CH$_2$, —C=NR$^{32}$ or —C=N$^+$R$^{33}$R$^{34}$;
R$^{31}$ is hydrogen, alkyl$_{C1-10}$, alkene$_{C2-12}$, aryl or a photocleavable group;
R$^{32}$, R$^{33}$ and R$^{34}$, which may be the same or different, are each hydrogen, alkyl$_{C1-10}$, alkene$_{C2-12}$ or aryl;
m is an integer from 1 to 9;
with the proviso that when R$^1$ together with R$^6$ forms a ring II in which R$^7$ is hydrogen or alkyl C$_{1-10}$, X$_a$ is —C≡C— and X$_b$ is absent, then Y is not —CO$_2$R$^{13}$;
and isomers thereof;
in free or in salt form.

2. The compound according to claim 1 wherein A$^1$ is CR$^3$, A$^2$ is CR$^4$, A$^3$ is CR$^5$; and
R$^2$, R$^3$, R$^4$, and R$^5$ are each as defined in claim 1.

3. The compound according to claim 1 wherein R$^2$ is a group III:

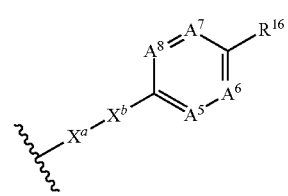

III wherein X$^a$ is —C≡C— and X$^b$ is —C≡C—; and
A$^5$, A$^6$, A$^7$, A$^8$ and R$^{16}$ are each as defined in claim 1.

4. The compound according to claim 3 wherein $X^b$ is absent and $X^a$ is selected from a group consisting of: —C≡C—, —CH=CH—, and —N=CH—.

5. The compound according to claim 3 wherein $A^5$ is $CR^{17}$, $A^6$ is $CR^{18}$, $A^7$ is $CR^{19}$ and $A^8$ is $CR^{20}$; and
$X^a$, $X^b$, $R^{16}$, $R^{17}$, $R^{18}$, $R^{19}$ and $R^{20}$ are each as defined in claim 1.

6. The compound according to claim 3 wherein $A^5$ is $CR^{17}$, $A^6$ is $CR^{18}$, $A^7$ is $CR^{19}$ and $A^8$ is $CR^{20}$; and
$R^{17}$, $R^{19}$ and $R^{20}$ are each as defined in claim 1;
$R^{16}$ together with $R^{18}$ forms a ring IV:

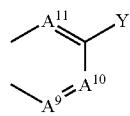

IV wherein $A^9$, $A^{10}$, $A^{11}$ and Y are each as defined in claim 1.

7. The compound according to claim 3 wherein $R^2$ is a group III;

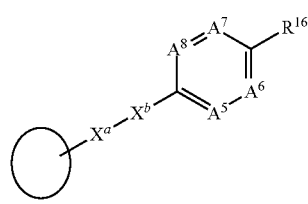

III and $R^{16}$ is —C≡C—$R^{23}$
wherein $R^{23}$ is a group V:

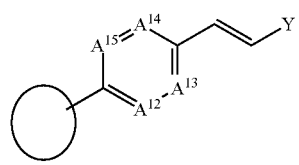

V in which
$A^{12}$ is $CR^{27}$, $A^{13}$ is $CR^{28}$, $A^{14}$ is $CR^{29}$ and $A^{15}$ is $CR^{30}$; and
$R^{27}$, $R^{28}$, $R^{29}$, $R^{30}$ and Y are each as defined in claim 1.

8. The compound according to claim 7 wherein $R^{16}$ is —C≡C—$R^{23}$, $R^{23}$ is a group V and Y is —$CO_2R^{31}$, —COH, —$CO_2CH_2$C≡CH, —CN, —$SF_5$, —$SO_3H$, —$SO_2NH_2$, —$SO_2CF_3$, in which $R^{31}$ is hydrogen, alkyl$_{C1-10}$, alkene$_{C2-12}$, aryl or a photocleavable group.

9. The compound according to claim 7 wherein Y is —$CO_2R^{31}$ in which $R^{31}$ is hydrogen, alkyl$_{C1-10}$, alkene$_{C2-12}$, aryl or a photocleavable group.

10. The compound according to claim 1 wherein $R^7$ is alkyl C1-10.

11. The compound according to claim 1 wherein $R^8$, $R^9$, $R^{10}$ and $R^{11}$ are each hydrogen.

12. The compound according to claim 1 wherein $R^8$ and $R^{10}$ or $R^9$ and $R^{11}$ represent a bond.

13. The compound according to claim 1 wherein $R^{12}$ and $R^{13}$ are the same or different; $R^{12}$ and $R^{13}$ may each represent alkyl C1-4.

14. The compound according to claim 1 wherein $R^2$ is selected from a group consisting of group VI:

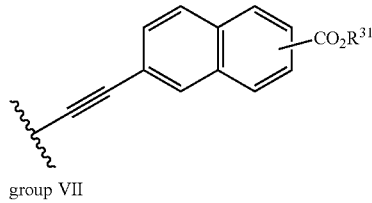

VI group VII

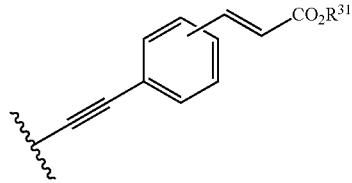

VII group VIII

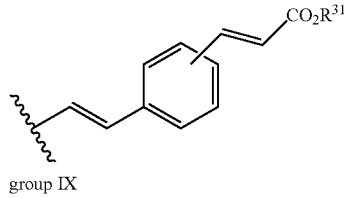

VIII and group IX

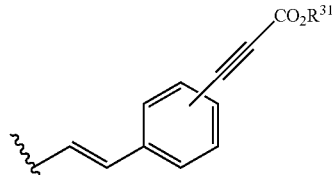

IX wherein $R^{31}$ is as defined in claim 1.

15. The compound of formula I according to claim 1 that is selected from the group consisting of:
(2E)-3-(4-2-[4,4-dimethyl-1-(propyn-2-yl)-1,2,3,4-tetrahydroquinolin-6-yl] ethynylphenyl)prop-2-enoic acid; and
(2E)-3-(4-2-[4,4-dimethyl-1-(propyn-2-yl)-1,2,3,4-tetrahydroquinolin-6-yl] ethynylphenyl)prop-2-enoic acid methyl ester;
and isomers thereof;
in free or in salt form.

16. A composition comprising the compound according to claim 1 in combination with one or more pharmaceutically acceptable excipients; said composition being for use in the generation of reactive oxygen species when said compound is activated by light.

17. The composition according to claim 16 for use in the treatment of one or more of a cancer selected from head and neck tumours, breast cancer, gynaecological tumours, brain tumours, colorectal cancer, prostate cancer, mesothelioma, and pancreatic cancer, or a disease caused by a pathogenic organism selected from bacteria, viruses, fungi, parasites, protozoa and toxins, as well as cells and tissues infected or infiltrated therewith.

* * * * *